United States Patent
Cooper et al.

(10) Patent No.: US 9,149,462 B2
(45) Date of Patent: *Oct. 6, 2015

(54) PYRAZOLE COMPOUNDS ACTING AGAINST ALLERGIC, INFLAMMATORY AND IMMUNE DISORDERS

(75) Inventors: Anthony William James Cooper, Stevenage (GB); Paul Martin Gore, Stevenage (GB); David House, Stevenage (GB)

(73) Assignee: Glaxo Group Limited, Brentford, Middlesex (GB)

( * ) Notice: Subject to any disclaimer, the term of this patent is extended or adjusted under 35 U.S.C. 154(b) by 65 days.

This patent is subject to a terminal disclaimer.

(21) Appl. No.: 13/879,652

(22) PCT Filed: Oct. 19, 2011

(86) PCT No.: PCT/EP2011/068221
§ 371 (c)(1),
(2), (4) Date: Apr. 16, 2013

(87) PCT Pub. No.: WO2012/052459
PCT Pub. Date: Apr. 26, 2012

(65) Prior Publication Data
US 2013/0217658 A1    Aug. 22, 2013

Related U.S. Application Data

(60) Provisional application No. 61/405,254, filed on Oct. 21, 2010.

(51) Int. Cl.
| A61K 31/415 | (2006.01) |
| A61K 45/06 | (2006.01) |
| A61K 31/4439 | (2006.01) |
| C07D 231/40 | (2006.01) |
| C07D 401/12 | (2006.01) |

(52) U.S. Cl.
CPC ........... *A61K 31/415* (2013.01); *A61K 31/4439* (2013.01); *A61K 45/06* (2013.01); *C07D 231/40* (2013.01); *C07D 401/12* (2013.01)

(58) Field of Classification Search
CPC .............................. C07D 231/40; C07D 401/12
See application file for complete search history.

(56) References Cited

U.S. PATENT DOCUMENTS

2013/0203705 A1 * 8/2013 Cooper et al. ................. 514/94

FOREIGN PATENT DOCUMENTS

| WO | WO 03/037274 A2 | 5/2003 |
| WO | WO 2010/122088 A1 | 10/2010 |
| WO | WO 2010/122089 A1 | 10/2010 |
| WO | WO 2012/052458 | 4/2012 |

OTHER PUBLICATIONS

Database Registry [online] chemical Abstracts Service, Columbus, Ohio, US; May 14, 2003, Benzamide, N-[1-[(2,4-dichlorophenyl)methyl]-1H-pyraz, XP 002663702, Database accession No. 515178-09-3, whole document.
Yonetoku Y. et al., "Novel Potent and selective calcium-release-activitated calcium (CRAC) channel inhibitors. Part 2: Synthesis and inhibitory activity of aryl-3-trifluoromethylpyrazoles", BioOrganic & Medicinal Chemistry, Pergamon, GB., vol. 14, No. 15, Aug. 1, 2006 pp. 5370-5383, XP025133434, ISSN: 0968-0896.
Yonetoku Y. et al., "Novel Potent and selective calcium-release-activitated calcium (CRAC) channel inhibitors. Part 1: Synthesis and inhibitory activity of 5-(1-methyl-3-trifluoromethyl-1H-pyrazol-5-yl)-2-thiophenecarboxamides", BioOrganic & Medicinal Chemistry, Pergamon, GB., vol. 14, No. 14, Jul. 15, 2006 pp. 4750-4760, XP025133377, ISSN: 0968-0896.
Yonetoku Y. et al., "Novel Potent and selective Ca<2+> release-activated Ca<2+> (CRAC) channel inhibitors. Part 3: Synthesis and CRAC channel inhibitory activity of 4'-[trifluoromethyl)pyrazol-1-yl]carboxan ilides", BioOrganic & Medicinal Chemistry, Pergamon, GB., vol. 16, No. 21, Nov. 1, 2008 pp. 9457-9466, XP025545771, ISSN: 0968-0896.
Hall A., et al., "Non-acidic pyrazole EP1 receptor antagonists with in vivo analgesic efficacy", BioOrganic & Medicinal Chemistry Letters, Pergamon, Elsevier Science, GB, vol. 18, No. 11, Jun. 1, 2008, pp. 3392-3399, XP022711234, ISSN: 0960-894X.

* cited by examiner

*Primary Examiner* — Kamal Saeed
(74) *Attorney, Agent, or Firm* — Linda E. Hall; John E. Lemanowicz

(57) ABSTRACT

The present invention relates to pyrazole amide derivatives pharmaceutical compositions containing these compounds and to their use in therapy.

10 Claims, No Drawings

PYRAZOLE COMPOUNDS ACTING AGAINST ALLERGIC, INFLAMMATORY AND IMMUNE DISORDERS

This application is a 371 of International Application No. PCT/EP2011/068221, filed 19 Oct. 2011, which claims the benefit of U.S. Provisional Application No. 61/405,254, filed 21 Oct. 2010, which is incorporated herein in its entirety.

FIELD OF THE INVENTION

The present invention relates to amide derivatives, pharmaceutical compositions containing these compounds and to their use in therapy. More particularly the present invention relates to pyrazole amide derivatives and their use in the treatment of a number of diseases, conditions or disorders such as allergic disorders, inflammatory disorders and disorders of the immune system.

BACKGROUND OF THE INVENTION

Calcium release activated calcium (CRAC) channels are a subset of store operated channels (SOC) which are opened in response to depletion of intracellular calcium stores and represent the critical point of calcium entry into certain cells such as mast cells and T-cells.

Two proteins have been identified as the essential components for CRAC channel function namely STIM1 (stromal interaction molecule 1), a calcium sensor localised in the endoplasmic reticulum, and ORAI1, a pore subunit of the CRAC channel that is gated by STIM1.

Small molecule inhibitors of the CRAC channel current (hereafter ICRAC inhibitors) are known in the art, their identification and therapeutic potential are described by Derler et al (Expert Opin. Drug Discovery; 2008; Vol. 3(7) pp. 787-800). U.S. Pat. No. 6,958,339 discloses a series of pyrazole derivatives that are said to possess calcium release-activated calcium channel inhibitory activity which are believed to be useful in the treatment of allergic, inflammatory or autoimmune diseases.

PCT patent application PCT/EP2010/055318 discloses a series of pyrazole amide compounds which are calcium release activated calcium channel (ICRAC) inhibitors.

SUMMARY OF THE INVENTION

A class of compounds has been found that are calcium release activated calcium channel (ICRAC) inhibitors.

In a first aspect of the present invention, there is provided a compound of formula (I) or a salt thereof, in particular a pharmaceutically acceptable salt thereof.

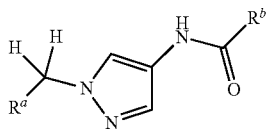
(I)

In a second aspect of the present invention, there is provided a pharmaceutical composition comprising a compound of formula (I) or a pharmaceutically acceptable salt thereof, and one or more pharmaceutically acceptable carriers, diluents or excipients.

In a third aspect of the present invention, there is provided a compound of formula (I) or a pharmaceutically acceptable salt thereof, for use in therapy, in particular in the treatment of a disease or condition for which an ICRAC inhibitor is indicated.

In a fourth aspect of the present invention, there is provided a method of treating a disease or condition for which an ICRAC inhibitor is indicated in a subject in need thereof which comprises administering a therapeutically effective amount of compound of formula (I) or a pharmaceutically acceptable salt thereof.

In a fifth aspect of the present invention, there is provided the use of a compound of formula (I) or a pharmaceutically acceptable salt thereof, in the manufacture of a medicament for the treatment of a disease or condition for which an ICRAC inhibitor is indicated.

DETAILED DESCRIPTION OF THE INVENTION

In a first aspect of the present invention, there is provided a compound of formula (I) thereof

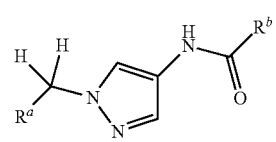
(I)

in which
$R^a$ is a group of formula (a1)

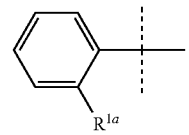
(a1)

in which
$R^{1a}$ is $CF_3$, $OCF_3$, $C_{1-6}$alkoxy or $R^{1a}$ is a group $L^1$-$Z^1$ in which $L^1$ is a bond, O, $CH_2$, $OCH_2$ or $CH_2O$ and $Z^1$ is aryl;
or $R^a$ is a group of formula (a2)

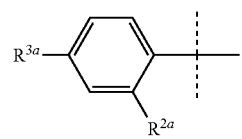
(a2)

in which
$R^{2a}$ is halogen or $OCH_2Ph$; and
$R^{3a}$ is Cl or Br;
or $R^a$ is a group of formula (a3)

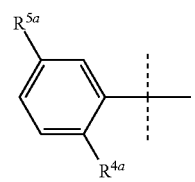
(a3)

in which
R$^{4a}$ is C$_{1-6}$alkoxy, CF$_3$ or OCH$_2$Ph; and
R$^{5a}$ is halogen;
or R$^a$ is a group of formula (a4)

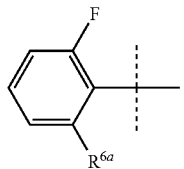

(a4)

in which
R$^{6a}$ is F, Br or CF$_3$;
R$^b$ is a group of formula (b)

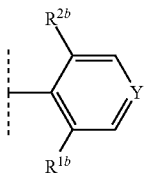

(b)

wherein
Y is CH or N,
R$^{1b}$ is halogen;
R$^{2b}$ is H, halogen or C$_{1-3}$alkyl;
or a salt thereof.

In one embodiment the compound of formula (I) is other than N-{1-[(2,4-dichlorophenyl)methyl]-1H-pyrazol-4-yl}-2,6-difluorobenzamide.

In one embodiment R$^a$ is a group of formula (a1) in which R$^{1a}$ is a group L$^1$-Z$^1$ wherein L$^1$ is as defined above and Z$^1$ is phenyl.

In one embodiment R$^a$ is a group of formula (a2) in which R$^{2a}$ and R$^{3a}$ are both chloro.

In one embodiment R$^a$ is a group of formula (a3) in which R$^{4a}$ is OCH$_2$Ph and R$^{5a}$ is halogen (such as chloro).

In a further embodiment R$^a$ is a group of formula (a4) in which R$^{6a}$ is CF$_3$ In one embodiment R$^b$ is a group of formula (b) in which Y is CH.

In one embodiment R$^b$ is a group of formula (b) in which R$^{1b}$ and R$^{2b}$ are both halogen (such as both fluoro).

In a yet further embodiment R$^b$ is a group of formula (b) in which Y is CH and R$^{1b}$ and R$^{2b}$ are both fluoro.

While the embodiments for each variable have generally been listed above separately for each variable this invention is intended to include all combinations of embodiments described hereinabove including salts thereof.

Specific examples include a compound selected from the group consisting of any one of examples 1-30 as defined herein, or a salt thereof.

In one embodiment there is provided (2,6-Difluoro-N-(1-{[2-fluoro-6-(trifluoromethyl)phenyl]methyl}-1H-pyrazol-4-yl)benzamide).

Throughout the present specification, unless otherwise stated:
the term "halogen" is used to describe a group selected from fluorine, chlorine, bromine or iodine;

the terms "C$_{1-3}$alkyl" and "C$_{1-6}$alkyl", whether alone or used as part of another group, is used to describe a group comprising a linear or branched alkyl group containing from 1 to 3 or 1 to 6 carbon atoms respectively; examples of such groups include methyl, ethyl, propyl, isopropyl, n-butyl, isobutyl, t-butyl, pentyl or hexyl.

the term "C$_{1-6}$alkoxy" is used to describe a group or a part of the group wherein an oxygen atom is bound to the rest of the molecule and to the above mentioned C$_{1-6}$alkyl group; examples of such groups include methoxy, ethoxy, propoxy, isopropoxy, n-butoxy, isobutoxy, t-butoxy, pentoxy or hexoxy;

The term "aryl" is used to describe an aromatic hydrocarbon ring such as phenyl and naphthyl. Such aryl groups may be optionally substituted by one of more substituents (e.g. two or three, which may be the same or different) selected from the group consisting of halogen, C$_{1-6}$alkyl, or C$_{1-6}$alkoxy;

It is believed that the compounds of formula (I) may have one or more ADMET properties which may make it particularly suitable for development as a pharmaceutical.

It will be appreciated that the present invention covers compounds of formula (I) as the free base and as salts thereof. Because of their potential use in medicine, salts of the compounds of formula (I) are desirably pharmaceutically acceptable. Suitable pharmaceutically acceptable salts can include acid or base addition salts. As used herein, the term 'pharmaceutically acceptable salt' means any pharmaceutically acceptable salt of a compound of formula (I) (in stoichiometric or non-stoichiometric form). For a review on suitable salts see Berge et al., J. Pharm. Sci., 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

Pharmaceutically acceptable acid addition salts include hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

Other non-pharmaceutically acceptable salts, e.g. formates, oxalates or trifluoroacetates, may be used, for example in the isolation of the compounds of formula (I), and are included within the scope of this invention.

In one embodiment the compound of formula (I) is in the form of a free base.

The invention encompasses all prodrugs, of the compound of formula (I), which upon administration to the recipient is capable of providing (directly or indirectly) the compound of formula (I), or an active metabolite or residue thereof. Such prodrugs are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of such teaching, and to Rautio et al (Nature Reviews; 2008; Vol. 7, p 255-270). In one embodiment there is provided a compound of formula (I) or a prodrug thereof, or a salt thereof.

In one embodiment there is provided a prodrug of a compound of formula (I) which is a compound of formula (IA) or a pharmaceutically acceptable salt thereof

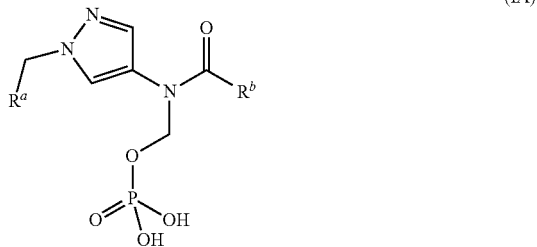

(IA)

wherein $R^a$ and $R^b$ are as defined in formula (I).

In one embodiment there is provided a prodrug of the compound (2,6-Difluoro-N-(1-{[2-fluoro-6-(trifluoromethyl)phenyl]methyl}-1H-pyrazol-4-yl)benzamide) which is a compound of formula (IB)

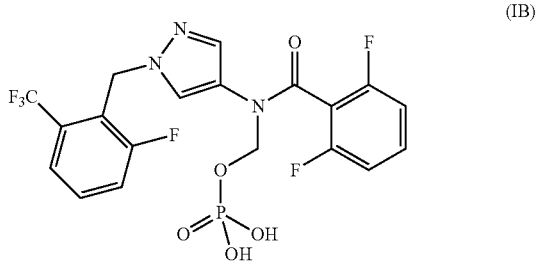 [SMILES: O=C(c1c(F)cccc1F)N(COP(=O)(O)O)c1cnn(Cc2c(F)cccc2C(F)(F)F)c1]

(IB)

or a pharmaceutically acceptable salt thereof.

Suitable pharmaceutically acceptable salts of the compound of formula (IA) and (IB) include alkali metal salts (such as sodium or potassium), alkaline earth metals (such as calcium and magnesium), ammonium salts and salts with organic bases, including salts of primary, secondary and tertiary amines, such as isopropylamine, diethylamine, ethanolamine, trimethylamine, dicyclohexyl amine and N-methyl-D-glucamine.

In one embodiment the compound of formula (IA) or (IB) is in the form of a pharmaceutically acceptable salt (such as a di-sodium salt).

In a further embodiment there is provided isotopically labelled compounds of formula (i) in particular the following formula (1')

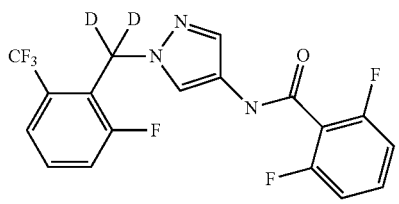 [SMILES: [2H]C([2H])(c1c(F)cccc1C(F)(F)F)n1cc(NC(=O)c2c(F)cccc2F)cn1]

Or a prodrug thereof or a pharmaceutically acceptable salt thereof.

Included within the scope of the "a compound of formula (I)" are all solvates (including hydrates), complexes, polymorphs, prodrugs, radiolabelled derivatives, of the compound of formula (I) and pharmaceutically acceptable salts thereof.

The invention also includes isotopically-labelled compounds of formula (I), which are identical to the compounds of formula (I) and salts thereof, but for the fact that one or more atoms are replaced by an atom having an atomic mass or mass number different from the atomic mass or mass number most commonly found in nature. Substitution with heavier isotopes, for example deuterium i.e. 2H can afford certain therapeutic advantages resulting from greater metabolic stability, for example increased in vivo half life or reduced dosage requirements and hence may be preferred in some circumstances.

Examples of isotopes that can be incorporated into the compounds of the invention include isotopes of hydrogen, carbon, nitrogen, oxygen and fluorine, such as 2H, 3H, 11C, 14C and 18F.

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, N-methylpyrrolidinone, methanol and ethanol may be used to form solvates. Methods for identification of solvates include, but are not limited to, NMR and microanalysis. Solvates of the compounds of formula (I) are within the scope of the invention.

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

Certain of the compounds described herein may contain one or more chiral atoms so that optical isomers, e.g.—enantiomers or diastereoisomers may be formed. Accordingly, the present invention encompasses isomers of the compounds of formula (I) whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Separation of isomers may be achieved by conventional techniques known to those skilled in the art, e.g. by fractional crystallisation, chromatography or HPLC.

It will be understood that the present invention encompasses all tautomers of the compounds of formula (I) whether as individual tautomers or as mixtures thereof.

It will be appreciated from the foregoing that included within the scope of the invention are solvates, isomers and polymorphic forms of the compounds of formula (I) and salts thereof.

The compounds of formula (I) may be made by a variety of methods, including standard chemistry. Any previously defined variable will continue to have the previously defined meaning unless otherwise indicated. Illustrative general synthetic methods are set out below and then specific compounds of the invention are prepared in the working Examples.

In a further aspect the present invention provides a process for the preparation of a compound of formula (I) which is a process selected from (a), (b) and (c) in which:

(a) comprises the reaction of a compound of formula (II)

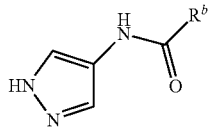

in which $R^b$ is as defined in formula (I) with a compound of formula (III)

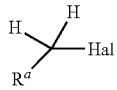

in which $R^a$ is as defined in formula (I) and Hal is halogen;
(b) comprises the reaction of a compound of formula (IV)

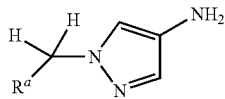

in which $R^a$ is as defined in formula (I) with a compound of formula (V) or an activated derivative thereof

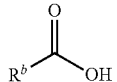

in which $R^b$ is as defined in formula (I)
(c) comprises converting a compound of formula (I) into a prodrug of a compound of formula (I)
Process (a)
For compounds of formula (III) a suitable Hal group is bromine. The reaction between the compounds of formula (II) and (III) may be carried out in an inert organic solvent such as tetrahydrofuran or dimethylformamide at ambient or elevated temperature, optionally in the presence of a suitable base such as potassium or caesium carbonate or a strong base (such as sodium t-butoxide or lithium bis(trimethylsilyl)amide (LiHMDS)).

The compounds of formula (II) may be prepared from 4-nitro-1H-pyrazole (which is commercially available) which may be hydrogenated to provide 1H-pyrazol-4-amine and then subsequently reacted with the appropriate acid chloride derivative using standard methodology. The compounds of formula (III) are prepared by methods described herein, by analogous methods thereto or are obtainable from commercial sources.
Process (b)
The compounds of formula (IV) and carboxylic acid of formula (V) are typically reacted under amide forming conditions that are familiar to those skilled in the art. Such reactions may be carried out in a suitable organic solvent (e.g. DMF or acetonitrile) with an amine (e.g. DIPEA or triethylamine) in the presence of a suitable activating group (e.g. HATU or TBTU).

The reaction may also be carried using an activated derivative of a compound of formula (V) such as an acid chloride. The reaction between an activated compound of formula (V) and a compound of formula (IV) is typically carried out in an inert organic solvent such as tetrahydrofuran, chloroform or dichloromethane or a mixed organic/aqueous system at ambient or elevated temperature, optionally in the presence of a suitable base e.g. an organic base (such as triethylamine or DIPEA), an alkali metal carbonate (such as potassium carbonate) or a alkali metal hydrogen carbonate (such as sodium hydrogen carbonate).
Process (c)
Compounds of formula (I) can be converted to compounds of formula (IA) by reaction with a suitable reagent such as chloromethyl bis(1,1-dimethylethyl)phosphate and subsequent deprotection of the resulting product using procedures described herein or by analogous methods thereto.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly. In some instances it may be appropriate to use protecting groups to prevent reactions between one or more groups or moieties. Such procedures are familiar to those skilled in the art (see, for example, "Protective groups in organic synthesis" by T. W. Greene and P. G. M. Wuts (John Wiley & sons 1999) or "Protecting Groups" by P. J. Kocienski (Georg Thieme Verlag 1994).

It will be further appreciated that novel intermediates described herein may also form another aspect of the present invention.

The compounds of formula (I) and salts thereof are believed to be calcium release activated calcium channel inhibitors, and thus be potentially useful in the treatment of diseases or conditions for which such a compound is indicated.

The present invention thus provides a compound of formula (I) or a pharmaceutically acceptable salt thereof, for use in therapy.

The present invention thus provides a compound of formula (I) or a pharmaceutically acceptable salt thereof, for use in the treatment of diseases or conditions for which an ICRAC inhibitor is indicated.

Also provided is the use of a compound of formula (I) or a pharmaceutically acceptable salt thereof, in the manufacture of a medicament for the treatment of diseases or conditions for which an ICRAC inhibitor is indicated.

Also provided is a method of treating diseases or conditions for which an ICRAC inhibitor is indicated in a subject in need thereof which comprises administering a therapeutically effective amount of compound of formula (I) or a pharmaceutically acceptable salt thereof.

In one embodiment the subject in need thereof is a mammal, such as a human.

As used herein, the term "effective amount" means that amount of a drug or pharmaceutical agent that will elicit the biological or medical response of a tissue, system, mammal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Calcium release activated calcium channel inhibitors (i.e. ICRAC inhibitors) are believed to be indicated in the treatment and/or prophylaxis of a variety of diseases, conditions or disorders in mammals such as humans. These include allergic disorders, inflammatory disorders, disorders of the immune system and conditions in which anti-platelet or anti-thrombotic activity is useful.

Examples of allergic disorders include: rhinitis (such as allergic rhinitis), sinusitis, rhinosinusitis, chronic or recurrent otitis media, drug reactions, insect sting reactions, latex allergy, conjunctivitis, urticaria, anaphylaxis and anaphylactoid reactions, atopic dermatitis and food allergies.

Examples of inflammatory disorders include: inflammatory lung disorders (such as asthma, acute respiratory distress syndrome, acute lung injury, chronic obstructive pulmonary disease, bronchiectasis and cystic fibrosis); chronic inflammatory disorders of joints (such as arthritis, rheumatoid arthritis, osteoarthritis and bone diseases associated with increased bone resorption); inflammatory bowel diseases (such as Barrett's oesophagus, ileitis, ulcerative colitis and Crohn's disease); inflammatory disorders of the eye (such as corneal dystrophy, trachoma, uveitis, sympathetic ophthalmitis and endophthalmitis); inflammatory diseases of the kidney (such as glomerulonephritis, nephrosis, nephritic syndrome and IgA nephropathy); inflammatory disorders of the skin (such as psoriasis and eczema); inflammatory diseases of the central nervous system (such as chronic demyelinating diseases of the nervous system, multiple sclerosis, AIDS-related neurodegeneration and Alzheimers disease, infectious meningitis, enceophalomyelitis, Parkinson's disease, Huntington's disease, amyotrophic lateral sclerosis and viral or autoimmune encephalitis); inflammatory diseases of the heart (such as myocarditis and cardiomyopathy, ischemic heart disease, myocardial infarction and atherosclerosis); other diseases with significant inflammatory components, including tuberculosis; leprosy; rejection of transplants; pre-eclampsia; endometriosis, chronic liver failure; brain and spinal cord trauma and cancer; and conditions where systemic inflammation of the body may also be present (such as septic shock, hemorrhagic or anaphylactic shock or shock induced by cancer chemotherapy).

Examples of disorders of the immune system include: autoimmune diseases of the central and peripheral nervous system (such as multiple sclerosis, myasthenia gravis, Eaton-Lambert Myasthenic syndrome); autoimmune neurophathies (such as Guillain-Barré,); autoimmune diseases of the eye (such as autoimmune uveitis); autoimmune diseases of the blood (such as autoimmune haemolytic anemia, pernicious anemia, and autoimmune thrombocytopenia e.g. Idiopathic Thrombocytopaenic Purpura); autoimmune diseases of the vasculature (such as temporal arteritis, anti-phospholipid syndrome, vasculitides e.g. Wegener's granulomatosis and Behcet's disease); autoimmune diseases of the skin (such as alopecia greata, psoriasis, dermatitis herpetiformis, pemphigus vulgaris, bullous pemphigoid and vitiligo); autoimmune disease of the gastrointestinal tract (such as coeliac disease, Crohn's disease, ulcerative colitis, primary biliary cirrhosis and autoimmune hepatitis); autoimmune disorders of the endocrine glands (such as Type1 diabetes mellitus, autoimmune thyroiditis, Grave's disease, Hashimoto's thyroiditis, autoimmune oophoritis and orchitis); autoimmune disorder of the adrenal gland (such as Addisons disease); and multi system autoimmune diseases including connective tissue and musculoskeletal system diseases (such as rheumatoid arthritis, systemic lupus erythematosus, scleroderma, polymyositis, dermatomyositis), spondyloarthropathies (such as ankylosing spondylitis and psoriatic arthritis).

Examples of conditions where anti-platelet or anti-thrombotic activity is useful for treatment and/or prophylaxis include: ischemic heart disease, myocardial infarction, cerebrovascular accident (stroke) and vascular thrombosis (venous, arterial and intra-cardiac).

Further diseases or conditions which may be treated by the compounds of the invention include conditions where mast cells and basophils contribute to pathology, such as mast cell leukaemia, mastocytosis, endometriosis and basophil leukaemia.

The term "disease or condition for which an ICRAC inhibitor is indicated", is intended to include each of or all of the above disease states.

It is believed that the compounds of formula (I), having ICRAC inhibitory activity, may inhibit mast cell degranulation and/or inhibit T cell activation. Compounds having such activity may be particularly suitable for the treatment of a number of diseases and conditions, for example asthma and rhinitis.

In one embodiment the disease or condition for which an ICRAC inhibitor is indicated is asthma.

In a further embodiment the disease or condition for which an ICRAC inhibitor is indicated is rhinitis While it is possible that for use in therapy, a compound of formula (I) as well as pharmaceutically acceptable salts thereof may be administered as the raw chemical, it is typical to formulate in a suitable composition comprising one or more pharmaceutically acceptable carriers, diluents or excipients. Such compositions may be prepared using standard procedures.

Thus, there is provided a pharmaceutical composition which comprises a compound of formula (I) or a pharmaceutically acceptable salt thereof, and one or more pharmaceutically acceptable carriers, diluents and/or excipients.

Thus there is provided a pharmaceutical composition for the treatment of diseases or conditions in which an ICRAC inhibitor is indicated comprising a compound of formula (I) or a pharmaceutically acceptable salt thereof.

A pharmaceutical composition comprising a compound of formula (I) or a pharmaceutically acceptable salt thereof, which may be prepared by admixture, suitably at ambient temperature and atmospheric pressure, may be suitable for topical administration (which includes epicutaneous, inhaled, intranasal or ocular administration), enteral administration (which includes oral or rectal administration) or parenteral administration (such as by injection or infusion). Of interest are compositions comprising a compound of formula (I) or a pharmaceutically acceptable salt thereof, suitable for topical administration, particularly suitable for intranasal administration.

Generally, compositions may be in the form of solutions or suspensions (aqueous or non-aqueous), tablets, capsules, oral liquid preparations, powders, granules, lozenges, lotions, creams, ointments, gels, foams, reconstitutable powders or suppositories as required by the route of administration.

Generally, the compositions comprising a compound of formula (I) or a pharmaceutically acceptable salt thereof may contain from about 0.1% to 99% (w/w), such as from about 10 to 60% (w/w) (based on the total weight of the composition), of the compound of formula (I) or the pharmaceutically acceptable salt thereof, depending on the route of administration. The dose of the compound used in the treatment of the aforementioned diseases will vary in the usual way with the seriousness of the diseases, the weight of the sufferer, and other similar factors. However, as a general guide, suitable unit doses may be about 0.05 to 1000 mg, for example about 0.05 to 200 mg, and such unit doses may be administered more than once a day, for example two or three times a day or as desired. Such therapy may extend for a number of weeks or months.

Further provided is a pharmaceutical composition for the treatment of a disease or condition for which an ICRAC inhibitor is indicated comprising a compound of formula (I) or a pharmaceutically acceptable salt thereof. In one embodiment there is provided a pharmaceutical composition for the treatment of an allergic disorder (such as rhinitis) or an inflammatory disorder (such as asthma) comprising a compound of formula (I) or prodrug thereof, or a pharmaceutically acceptable salt thereof.

Thus there is provided a pharmaceutical composition comprising 0.05 to 1000 mg of a compound of formula (I), or a pharmaceutically acceptable salt thereof, and 0.1 to 2 g of one or more pharmaceutically acceptable carriers, diluents and/or excipients.

The proportion of the compound of formula (I) or a pharmaceutically acceptable salt thereof, in a topical composition will depend on the precise type of composition to be prepared and the particular route of administration, but will generally be within the range of from about 0.001 to 10% (w/w), based on the total weight of the composition. Generally, however for most types of preparations the proportion used will be within the range of from about 0.005 to 1% (w/w), such as about 0.01 to 1% (w/w), for example about 0.01 to 0.5% (w/w), based on the total weight of the composition. However, in powders for inhalation the proportion used will generally be within the range of from about 0.1 to 5% (w/w), based on the total weight of the composition.

Generally, pharmaceutical compositions suitable for intranasal or inhaled administration may conveniently be formulated as aerosols, solutions, suspensions, drops, gels or dry powders, with one or more pharmaceutically acceptable carriers and/or excipients such as aqueous or non-aqueous vehicles, thickening agents, isotonicity adjusting agents, antioxidants and/or preservatives.

For compositions suitable for intranasal or inhaled administration, the compound of formula (I) or a prodrug thereof, or a pharmaceutically acceptable salt thereof, may typically be in a particle-size-reduced form, which may be prepared by conventional techniques, for example, micronisation and milling. Generally, the size-reduced (e.g. micronised) compound of formula (I) or a prodrug thereof, or a pharmaceutically acceptable salt thereof, can be defined by a $D_{50}$ value of about 0.5 to 10 microns, such as of about 2 to 4 microns (for example as measured using laser diffraction).

In one aspect, pharmaceutical compositions comprising a compound of formula (I) or a pharmaceutically acceptable salt thereof are suitable for intranasal administration. Intranasal compositions comprising a compound of formula (I) or a pharmaceutically acceptable salt thereof, may permit the compound(s) to be delivered to all areas of the nasal cavities (the target tissue) and further, may permit the compound(s) to remain in contact with the target tissue for longer periods of time. A suitable dosing regime for intranasal compositions would be for the patient to inhale slowly through the nose subsequent to the nasal cavity being cleared. During inhalation the composition would be administered to one nostril while the other is manually compressed. This procedure would then be repeated for the other nostril. Typically, one or two sprays per nostril would be administered by the above procedure up to two or three times each day, ideally once daily. Of particular interest are intranasal compositions suitable for once daily administration.

Intranasal compositions may optionally contain one or more suspending agents, one or more preservatives, one or more wetting agents and/or one or more isotonicity adjusting agents as desired. Compositions suitable for intranasal administration may optionally further contain other excipients, such as antioxidants (for example sodium metabisulphite), taste-masking agents (such as menthol) and sweetening agents (for example dextrose, glycerol, saccharin and/or sorbitol).

The suspending agent, if included, will typically be present in the intranasal composition in an amount of between about 0.1 and 5% (w/w), such as between about 1.5% and 2.4% (w/w), based on the total weight of the composition. Examples of suspending agents include Avicel®, carboxymethylcellulose, veegum, tragacanth, bentonite, methylcellulose and polyethylene glycols, e.g. microcrystalline cellulose or carboxy methylcellulose sodium. Suspending agents may also be included in compositions suitable for inhaled, ocular and oral administration as appropriate.

For stability purposes, intranasal compositions comprising a compound of formula (I) or a pharmaceutically acceptable salt thereof may be protected from microbial or fungal contamination and growth by inclusion of a preservative. Examples of pharmaceutically acceptable anti-microbial agents or preservatives may include quaternary ammonium compounds (e.g. benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid), chelating agents such as disodium ethylenediaminetetraacetate (EDTA) and other anti-microbial agents such as chlorhexidine, chlorocresol, sorbic acid and its salts (such as potassium sorbate) and polymyxin. Examples of pharmaceutically acceptable anti-fungal agents or preservatives may include sodium benzoate. The preservative, if included, may be present in an amount of between about 0.001 and 1% (w/w), such as about 0.015% (w/w), based on the total weight of the composition. Preservatives may be included in compositions suitable for other routes of administration as appropriate.

Compositions which contain a suspended medicament may include a pharmaceutically acceptable wetting agent which functions to wet the particles of medicament to facilitate dispersion thereof in the aqueous phase of the composition. Typically, the amount of wetting agent used will not cause foaming of the dispersion during mixing. Examples of wetting agents include fatty alcohols, esters and ethers, such as polyoxyethylene (20) sorbitan monooleate (Polysorbate 80). The wetting agent may be present in intranasal compositions in an amount of between about 0.001 and 0.05% (w/w), for example about 0.025% (w/w), based on the total weight of the composition. Wetting agents may be included in compositions suitable for other routes of administration, e.g. for inhaled and/or ocular administration, as appropriate.

An isotonicity adjusting agent may be included to achieve isotonicity with body fluids e.g. fluids of the nasal cavity, resulting in reduced levels of irritancy. Examples of isotonicity adjusting agents include sodium chloride, dextrose, xylitol and calcium chloride. An isotonicity adjusting agent may be included in intranasal compositions in an amount of between about 0.1 and 10% (w/w), such as about 5.0% (w/w), based on the total weight of the composition. Isotonicity adjusting agents may also be included in compositions suitable for other routes of administration, for example in compositions suitable for inhaled, ocular, oral liquid and parenteral administration, as appropriate.

Further, the intranasal compositions comprising a compound of formula (I), or a prodrug thereof, or a pharmaceutically acceptable salt thereof, may be buffered by the addition of suitable buffering agents such as sodium citrate, citric acid, phosphates such as disodium phosphate (for example the dodecahydrate, heptahydrate, dihydrate and anhydrous forms) or sodium phosphate and mixtures thereof. Buffering agents may also be included in compositions suitable for other routes of administration as appropriate.

Compositions for administration topically to the nose or lung for example, for the treatment of rhinitis, include pressurised aerosol compositions and aqueous compositions delivered to the nasal cavities by pressurised pump. Compositions which are non-pressurised and adapted to be administered topically to the nasal cavity are of particular interest. Suitable compositions contain water as the diluent or carrier for this purpose. Aqueous compositions for administration to the lung or nose may be provided with conventional excipients such as buffering agents, tonicity modifying agents and the like. Aqueous compositions may also be administered to the nose by nebulisation.

A fluid dispenser may typically be used to deliver a fluid composition to the nasal cavities. The fluid composition may be aqueous or non-aqueous, but typically aqueous. Such a fluid dispenser may have a dispensing nozzle or dispensing orifice through which a metered dose of the fluid composition is dispensed upon the application of a user-applied force to a pump mechanism of the fluid dispenser. Such fluid dispensers are generally provided with a reservoir of multiple metered doses of the fluid composition, the doses being dispensable upon sequential pump actuations. The dispensing nozzle or orifice may be configured for insertion into the nostrils of the user for spray dispensing of the fluid composition into the nasal cavity. A fluid dispenser of the aforementioned type is described and illustrated in WO05/044354 the entire content of which is hereby incorporated herein by reference. The dispenser has a housing which houses a fluid discharge device having a compression pump mounted on a container for containing a fluid composition. The housing has at least one finger-operable side lever which is movable inwardly with respect to the housing to cam the container upwardly in the housing to cause the pump to compress and pump a metered dose of the composition out of a pump stem through a nasal nozzle of the housing. In one embodiment, the fluid dispenser is of the general type illustrated in FIGS. 30-40 of WO05/044354.

In one aspect, there is provided an intranasal composition comprising a compound of formula (I) or a pharmaceutically acceptable salt thereof. In another aspect, such an intranasal composition is benzalkonium chloride-free.

Inhaled administration involves topical administration to the lung, such as by aerosol or dry powder composition.

Aerosol compositions suitable for inhaled administration may comprise a solution or fine suspension of the compound in a pharmaceutically acceptable aqueous or non-aqueous solvent. Aerosol compositions suitable for inhalation can be either a suspension or a solution and generally contain a compound of formula (I) or a prodrug thereof, or a pharmaceutically acceptable salt thereof, and a suitable propellant such as a fluorocarbon or hydrogen-containing chlorofluorocarbon or mixtures thereof, such as hydrofluoroalkanes, e.g. 1,1,1,2-tetrafluoroethane, 1,1,1,2,3,3,3-heptafluoro-n-propane or a mixture thereof. The aerosol composition may optionally contain additional excipients well known in the art such as surfactants or cosolvents. Examples of surfactants include, but are not limited to oleic acid, lecithin, an oligolactic acid or derivative e.g. as described in WO94/21229 and WO98/34596. An example of a cosolvent includes, but is not limited to ethanol. Aerosol compositions may be presented in single or multidose quantities in sterile form in a sealed container, which may take the form of a cartridge or refill for use with an atomising device or inhaler. Alternatively, the sealed container may be a unitary dispensing device such as a single dose nasal inhaler or an aerosol dispenser fitted with a metering valve (metered dose inhaler), which is intended for disposal once the contents of the container have been exhausted.

Dry powder inhalable compositions may take the form of capsules and cartridges of, for example, gelatine, or blisters of, for example, laminated aluminium foil, for use in an inhaler or insufflator. Such compositions may be formulated comprising a powder mix of a compound of formula (I) or a pharmaceutically acceptable salt thereof and a suitable powder base such as lactose or starch.

Optionally, for dry powder inhalable compositions, a composition suitable for inhaled administration may be incorporated into a plurality of sealed dose containers (e.g. comprising the dry powder composition) mounted longitudinally in a strip or ribbon inside a suitable inhalation device. The container is rupturable or peel-openable on demand and the dose of e.g. the dry powder composition may be administered by inhalation via the device such as the DISKUS™ device, marketed by GlaxoSmithKline. The DISKUS™ inhalation device is for example described in GB 2242134 A, and in such a device, at least one container for the composition in powder form (the container or containers may, for example, be a plurality of sealed dose containers mounted longitudinally in a strip or ribbon) is defined between two members peelably secured to one another; the device comprises: a means of defining an opening station for the said container or containers; a means for peeling the members apart at the opening station to open the container; and an outlet, communicating with the opened container, through which a user can inhale the composition in powder form from the opened container.

Aerosol compositions are typically arranged so that each metered dose or "puff" of aerosol contains about 20 µg-2000 µg, particularly about 20 µg-500 µg of a compound of formula (I) or a pharmaceutically acceptable salt thereof. Administration may be once daily or several times daily, for example 2, 3, 4 or 8 times, giving for example 1, 2 or 3 doses each time. The overall daily dose with an aerosol will be within the range of about 100 µg-10 mg, such as between about 200 µg-2000 µg. The overall daily dose and the metered dose delivered by capsules and cartridges in an inhaler or insufflator will generally be double those with aerosol compositions.

In another aspect, there is provided a pharmaceutical composition comprising a compound of formula (I) or a pharmaceutically acceptable salt thereof, which is suitable for epicutaneous administration. An epicutaneous composition to be applied to the affected area e.g. the skin, by one or more application per day, may be in the form of, for example, an ointment, a cream, an emulsion, a lotion, a foam, a spray, an aqueous gel, or a microemulsion. Such compositions may optionally contain one or more solubilising agents, skin-penetration-enhancing agents, surfactants, fragrances, preservatives or emulsifying agents.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents. Lotions may be formulated with an aqueous or oily base and will in general also contain one or more emulsifying agents, stabilising agents, dispersing agents, suspending agents or thickening agents.

In another aspect, there is provided a pharmaceutical composition comprising a compound of formula (I) or a pharmaceutically acceptable salt thereof, which is suitable for ocular administration. Such compositions may optionally contain one or more suspending agents, one or more preservatives, one or more wetting/lubricating agents and/or one or more isotonicity adjusting agents. Examples of ophthalmic wetting/lubricating agents may include cellulose derivatives, dextran 70, gelatin, liquid polyols, polyvinyl alcohol and povidone such as cellulose derivatives and polyols.

In another aspect, there is provided a pharmaceutical composition comprising a compound of formula (I) or a pharmaceutically acceptable salt thereof, which is suitable for oral administration. Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

In another aspect, there is provided a pharmaceutical composition comprising a compound of formula (I) or a prodrug thereof, or a pharmaceutically acceptable salt thereof, which is suitable for parenteral administration. Fluid unit dosage forms suitable for parenteral administration may be prepared utilising a compound of formula (I) or pharmaceutically acceptable salt thereof and a sterile vehicle which may be aqueous or oil based. The compound, depending on the vehicle and concentration used, may be either suspended or dissolved in the vehicle. In preparing solutions, the compound may be dissolved for injection and filter sterilised before filling into a suitable vial or ampoule and sealing. Optionally, adjuvants such as a local anaesthetic, preservatives and buffering agents may be dissolved in the vehicle. To enhance the stability, the composition may be frozen after filling into the vial and the water removed under vacuum. The lyophilised parenteral composition may be reconstituted with a suitable solvent just prior to administration. Parenteral suspensions may be prepared in substantially the same manner, except that the compound is suspended in the vehicle instead of being dissolved, and sterilisation cannot be accomplished by filtration. The compound may be sterilised by exposure to ethylene oxide before suspension in a sterile vehicle. A surfactant or wetting agent may be included in the composition to facilitate uniform distribution of the compound.

The compounds and pharmaceutical compositions according to the invention may be used in combination with or include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents such as antibiotics or antivirals, or antihistamines. The invention thus provides, in a further aspect, a combination comprising a compound of formula (I) or a pharmaceutically acceptable salt thereof, together with one or more other therapeutically active agents, for example selected from an anti-inflammatory agent such as a corticosteroid or an NSAID, an anticholinergic agent, a $\beta_2$-adrenoreceptor agonist, an antiinfective agent such as an antibiotic or an antiviral, or an antihistamine. One embodiment of the invention encompasses combinations comprising a compound of formula (I) or a pharmaceutically acceptable salt thereof together with a $\beta_2$-adrenoreceptor agonist, and/or an anticholinergic, and/or a PDE-4 inhibitor, and/or an antihistamine.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

The invention provides, in another aspect, a combination comprising a compound of formula (I) or a prodrug thereof, or a pharmaceutically acceptable salt thereof, together with a $\beta_2$-adrenoreceptor agonist.

Examples of $\beta_2$-adrenoreceptor agonists include salmeterol (which may be a racemate or a single enantiomer such as the R-enantiomer), salbutamol (which may be a racemate or a single enantiomer such as the R-enantiomer), formoterol (which may be a racemate or a single diastereomer such as the R,R-diastereomer), salmefamol, fenoterol, carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment the $\beta_2$-adrenoreceptor agonists are long-acting $\beta_2$-adrenoreceptor agonists, for example, compounds which provide effective bronchodilation for about 12 hours or longer. A further example of a $\beta_2$-adrenoreceptor agonist is the compound 4-{(1R)-2-[(6-{2-[(2,6-dichlorophenyl)methoxy]ethoxy}hexyl)amino]-1-hydroxyethyl}-2-(hydroxyethyl)phenol triphenylacetete (Vilanterol Trifenacetate).

Other $\beta_2$-adrenoreceptor agonists include those disclosed in WO02/066422, WO02/070490, WO02/076933, WO03/024439, WO03/072539, WO03/091204, WO04/016578, WO04/022547, WO04/037807, WO04/037773, WO04/037768, WO04/039762, WO04/039766, WO01/42193 and WO03/042160.

Examples of $\beta_2$-adrenoreceptor agonists include:
3-(4-{[6-({(2R)-2-hydroxy-2-[4-hydroxy-3-(hydroxymethyl)phenyl]ethyl}amino)hexyl]oxy}butyl)benzenesulfonamide;
3-(3-{[7-({(2R)-2-hydroxy-2-[4-hydroxy-3-hydroxymethyl)phenyl]ethyl}-amino) heptyl]oxy}propyl)benzenesulfonamide;
4-{(1R)-2-[(6-{2-[(2,6-dichlorobenzyl)oxy]ethoxy}hexyl) amino]-1-hydroxyethyl}-2-(hydroxymethyl)phenol;
4-{(1R)-2-[(6-{4-[3-(cyclopentylsulfonyl)phenyl] butoxy}hexyl)amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]ethyl]amino]ethyl]phenyl]formamide;

N-2{2-[4-(3-phenyl-4-methoxyphenyl)aminophenyl]ethyl}-2-hydroxy-2-(8-hydroxy-2(1H)-quinolinon-5-yl)ethylamine; and 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

The β$_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

The invention provides, in another aspect, a combination comprising a compound of formula (I) or a pharmaceutically acceptable salt thereof, together with a corticosteroid.

Suitable anti-inflammatory agents include corticosteroids. Examples of corticosteroids are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydro-furan-3S-yl)ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. In one embodiment corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β3-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Further examples of corticosteroids may include those disclosed in WO02/088167, WO02/100879, WO02/12265, WO02/12266, WO05/005451, WO05/005452, WO06/072599 and WO06/072600.

Non-steroidal compounds having glucocorticoid agonism that may possess selectivity for transrepression over transactivation and that may be useful in combination therapy include those disclosed in the following published patent applications and patents: WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651, WO03/08277, WO06/000401, WO06/000398, WO06/015870, WO06/108699, WO07/000,334 and WO07/054,294.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Examples of iNOS inhibitors include those disclosed in WO93/13055, WO98/30537, WO02/50021, WO95/34534 and WO99/62875. Examples of CCR3 inhibitors include those disclosed in WO02/26722.

The invention thus provides, in another aspect, a combination comprising a compound of formula (I) or a pharmaceutically acceptable salt thereof, together with a PDE4 inhibitor.

In one embodiment the invention provides the use of the compounds of formula (I) or a pharmaceutically acceptable salt thereof in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl) cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep., 1996; this patent and the compounds it discloses are incorporated herein in full by reference.

Other compounds include AWD-12-281 from Elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO04/024728 (Glaxo Group Ltd), WO04/056823 (Glaxo Group Ltd) and WO04/103998 (Glaxo Group Ltd).

The invention provides, in another aspect, a combination comprising a compound of formula (I) or a prodrug thereof or a pharmaceutically acceptable salt thereof together with an anticholinergic.

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$ receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Other anticholinergic agents include compounds which are disclosed in U.S. patent application 60/487,981 including, for example:
- (3-endo)-3-(2,2-di-2-thienylethenyl)-8,8-dimethyl-8-azoniabicyclo[3.2.1]octane bromide;
- (3-endo)-3-(2,2-diphenylethenyl)-8,8-dimethyl-8-azoniabicyclo[3.2.1]octane bromide;
- (3-endo)-3-(2,2-diphenylethenyl)-8,8-dimethyl-8-azoniabicyclo[3.2.1]octane 4-methylbenzenesulfonate;
- (3-endo)-8,8-dimethyl-3-[2-phenyl-2-(2-thienyl)ethenyl]-8-azoniabicyclo[3.2.1]octane bromide; and/or
- (3-endo)-8,8-dimethyl-3-[2-phenyl-2-(2-pyridinyl)ethenyl]-8-azoniabicyclo[3.2.1]octane bromide.

Further anticholinergic agents include compounds which are disclosed in U.S. patent application 60/511,009 including, for example:
- (endo)-3-(2-methoxy-2,2-di-thiophen-2-yl-ethyl)-8,8-dimethyl-8-azonia-bicyclo[3.2.1]octane iodide;
- 3-((endo)-8-methyl-8-aza-bicyclo[3.2.1]oct-3-yl)-2,2-diphenyl-propionitrile;
- (endo)-8-methyl-3-(2,2,2-triphenyl-ethyl)-8-aza-bicyclo[3.2.1]octane;
- 3-((endo)-8-methyl-8-aza-bicyclo[3.2.1]oct-3-yl)-2,2-diphenyl-propionamide;
- 3-((endo)-8-methyl-8-aza-bicyclo[3.2.1]oct-3-yl)-2,2-diphenyl-propionic acid;
- (endo)-3-(2-cyano-2,2-diphenyl-ethyl)-8,8-dimethyl-8-azonia-bicyclo[3.2.1]octane iodide;
- (endo)-3-(2-cyano-2,2-diphenyl-ethyl)-8,8-dimethyl-8-azonia-bicyclo[3.2.1]octane bromide;
- 3-((endo)-8-methyl-8-aza-bicyclo[3.2.1]oct-3-yl)-2,2-diphenyl-propan-1-ol;
- N-benzyl-3-((endo)-8-methyl-8-aza-bicyclo[3.2.1]oct-3-yl)-2,2-diphenyl-propionamide;
- (endo)-3-(2-carbamoyl-2,2-diphenyl-ethyl)-8,8-dimethyl-8-azonia-bicyclo[3.2.1]octane iodide;
- 1-benzyl-3-[3-((endo)-8-methyl-8-aza-bicyclo[3.2.1]oct-3-yl)-2,2-diphenyl-propyl]-urea;
- 1-ethyl-3-[3-((endo)-8-methyl-8-aza-bicyclo[3.2.1]oct-3-yl)-2,2-diphenyl-propyl]-urea;
- N-[3-((endo)-8-methyl-8-aza-bicyclo[3.2.1]oct-3-yl)-2,2-diphenyl-propyl]-acetamide;
- N-[3-((endo)-8-methyl-8-aza-bicyclo[3.2.1]oct-3-yl)-2,2-diphenyl-propyl]-benzamide;
- 3-((endo)-8-methyl-8-aza-bicyclo[3.2.1]oct-3-yl)-2,2-di-thiophen-2-yl-propionitrile;
- (endo)-3-(2-cyano-2,2-di-thiophen-2-yl-ethyl)-8,8-dimethyl-8-azonia-bicyclo[3.2.1]octane iodide;
- N-[3-((endo)-8-methyl-8-aza-bicyclo[3.2.1]oct-3-yl)-2,2-diphenyl-propyl]-benzenesulfonamide;
- [3-((endo)-8-methyl-8-aza-bicyclo[3.2.1]oct-3-yl)-2,2-diphenyl-propyl]-urea;
- N-[3-((endo)-8-methyl-8-aza-bicyclo[3.2.1]oct-3-yl)-2,2-diphenyl-propyl]-methanesulfonamide; and/or
- (endo)-3-{2,2-diphenyl-3-[(1-phenyl-methanoyl)-amino]-propyl}-8,8-dimethyl-8-azonia-bicyclo[3.2.1]octane bromide.

Further compounds include:
- (endo)-3-(2-methoxy-2,2-di-thiophen-2-yl-ethyl)-8,8-dimethyl-8-azonia-bicyclo[3.2.1]octane iodide;
- (endo)-3-(2-cyano-2,2-diphenyl-ethyl)-8,8-dimethyl-8-azonia-bicyclo[3.2.1]octane iodide;
- (endo)-3-(2-cyano-2,2-diphenyl-ethyl)-8,8-dimethyl-8-azonia-bicyclo[3.2.1]octane bromide;
- (endo)-3-(2-carbamoyl-2,2-diphenyl-ethyl)-8,8-dimethyl-8-azonia-bicyclo[3.2.1]octane iodide;
- (endo)-3-(2-cyano-2,2-di-thiophen-2-yl-ethyl)-8,8-dimethyl-8-azonia-bicyclo[3.2.1]octane iodide; and/or
- (endo)-3-{2,2-diphenyl-3-[(1-phenyl-methanoyl)-amino]-propyl}-8,8-dimethyl-8-azonia-bicyclo[3.2.1]octane bromide.

The invention thus provides, in another aspect, a combination comprising a compound of formula (I) or a prodrug thereof, or a pharmaceutically acceptable salt thereof, together with an antihistamine.

In one embodiment the invention provides a combination comprising a compound of formula (I), or a pharmaceutically acceptable salt thereof, together with an H1 antagonist. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a compound of formula (I), or a pharmaceutically acceptable salt thereof, together with an H3 antagonist (and/or inverse agonist). Examples of H3 antagonists include, for example, those compounds disclosed in WO2004/035556 and in WO2006/045416. Other histamine receptor antagonists which may be used in combination with the compounds of formula (I), or a pharmaceutically acceptable salt thereof, include antagonists (and/or inverse agonists) of the H4 receptor, for example, the compounds disclosed in Jablonowski et al., *J. Med. Chem.* 46:3957-3960 (2003).

The invention thus provides, in another aspect, a combination comprising a compound of formula (I) or a pharmaceutically acceptable salt thereof together with another calcium release activated calcium channel inhibitor.

The individual compounds of such combinations may be administered either sequentially or simultaneously in separate or combined pharmaceutical formulations. In one embodiment, the individual compounds will be administered simultaneously in a combined pharmaceutical composition. Appropriate doses of known therapeutic agents will readily be appreciated by those skilled in the art.

The combinations referred to above may conveniently be presented for use in the form of a pharmaceutical composition and thus pharmaceutical compositions comprising a combination as defined above together with one or more pharmaceutically acceptable carrier, diluents and/or excipient represent a further aspect of the invention.

The individual compounds of such combinations may be administered either sequentially in separate pharmaceutical compositions as well as simultaneously in combined pharmaceutical compositions. Additional therapeutically active ingredients may be suspended in the composition together with a compound of formula (I). Appropriate doses of known therapeutic agents will be readily appreciated by those skilled in the art.

The compounds of the invention may be prepared by the methods described below or by similar methods. Thus the following Intermediates and Examples serve to illustrate the preparation of the compounds of the invention, and are not to be considered as limiting the scope of the invention in any way.

EXAMPLES

General

Mass directed autopreparative HPLC was undertaken under the conditions given below. The UV detection was an averaged signal from wavelength of 210 nm to 350 nm and mass spectra were recorded on a mass spectrometer using alternate-scan positive and negative mode electrospray ionization.

Method A:
Method A was conducted on a Supelcosil ABZ+Plus column (typically 150 mm×30 mm i.d. 5 μm packing diameter) at ambient temperature. The solvents employed were:
A=0.1% v/v solution of formic acid in water
B=MeCN:Water 95:5+0.05% formic acid
Method B:
Method B was conducted on a Sunfire $C_{18}$ column (typically 150 mm×30 mm i.d. 5 μm packing diameter) at ambient temperature. The solvents employed were:
A=0.1% v/v solution of Formic acid in water
B=0.1% v/v solution of Formic acid in acetonitrile.
Method C:
Method C was conducted on a Sunfire $C_{18}$ column (typically 150 mm×30 mm i.d. 5 μm packing diameter) at ambient temperature. The solvents employed were:
A=0.1% v/v solution of trifluoroacetic acid in water
B=0.1% v/v solution of trifluoroacetic acid in acetonitrile.
Method D:
Method D was conducted on a Sunfire $C_{18}$ column (typically 100 mm×19 mm i.d. 5 μm packing diameter) at ambient temperature. The solvents employed were:
A=0.1% v/v solution of trifluoroacetic acid in water
B=0.1% v/v solution of trifluoroacetic acid in acetonitrile.
Method E:
Method E was conducted on an XBridge $C_{18}$ column (typically 150 mm×19 mm i.d. 5 μm packing diameter) at ambient temperature. The solvents employed were:
A=10 mM aqueous ammonium bicarbonate adjusted to pH 10 with ammonia solution.
B=acetonitrile.

Experimental Details

Experimental details of LC-MS systems 1-8 as referred to herein are as follows:

System 1
Column: 3.3 cm×4.6 mm ID, 3 μm ABZ+PLUS from Supelco®
Flow Rate: 3 ml/min.
Temp.: RT
UV detection range: 215 to 330 nm
Mass spectrum: Recorded on a mass spectrometer using alternative-scan positive and negative mode electrospray ionisation.
Solvents: A: 0.1% formic acid+10 mM ammonium acetate
B: 95% acetonitrile+0.05% formic acid
Gradient:

| Time (min.) | A % | B % |
|---|---|---|
| 0 | 100 | 0 |
| 0.7 | 100 | 0 |
| 4.2 | 0 | 100 |
| 4.6 | 0 | 100 |
| 4.8 | 100 | 0 |

System 2
Column: 50 mm×2.1 mm ID, 1.7 μm Acquity UPLC BEH $C_{18}$
Flow Rate: 1 ml/min.
Temp.: 40° C.
UV Detection Range: 220 to 330 nm
Mass spectrum: Recorded on a mass spectrometer using alternative-scan positive and negative mode electrospray ionisation.
Solvents: A: 0.1% formic acid+10 mM ammonium acetate
B: 95% acetonitrile+0.05% formic acid
Gradient:

| Time (min.) | A % | B % |
|---|---|---|
| 0 | 97 | 3 |
| 0.1 | 97 | 3 |
| 1.4 | 0 | 100 |
| 1.9 | 0 | 100 |
| 2 | 97 | 3 |

System 3
Column: 50 mm×2.1 mm ID, 1.7 μm Acquity UPLC BEH $C_{18}$
Flow Rate: 1 ml/min.
Temp.: 40° C.
UV Detection Range: 210 to 350 nm
Mass spectrum: Recorded on a mass spectrometer using alternative-scan positive and negative mode electrospray ionisation.
Solvents: A: 0.1% v/v formic acid in water
B: 0.1% v/v formic acid in acetonitrile Gradient:

| Time (min.) | A % | B % |
|---|---|---|
| 0 | 97 | 3 |
| 1.5 | 0 | 100 |
| 1.9 | 0 | 100 |
| 2.0 | 97 | 3 |

System 4
Column: 30 mm×4.6 mm ID, 3.5 μm Sunfire $C_{18}$ column
Flow Rate: 3 ml/min.
Temp.: 30° C.
UV Detection Range: 210 to 350 nm
Mass spectrum: Recorded on a mass spectrometer using alternative-scan positive and negative mode electrospray ionisation.
Solvents: A: 0.1% v/v solution of formic acid in water
B: 0.1% v/v solution of formic acid in acetonitrile
Gradient:

| Time (min.) | A % | B % |
|---|---|---|
| 0 | 97 | 3 |
| 0.1 | 97 | 3 |
| 4.2 | 0 | 100 |
| 4.8 | 0 | 100 |
| 4.9 | 97 | 3 |
| 5.0 | 97 | 3 |

System 5
Column: 50 mm×2.1 mm ID, 1.7 μm Acquity UPLC BEH $C_{18}$
Flow Rate: 1 ml/min.
Temp.: 40° C.
UV Detection Range: 220 to 330 nm
Mass spectrum: Recorded on a mass spectrometer using alternative-scan positive and negative mode electrospray ionisation.
Solvents: A: 0.1% v/v solution of trifluoroacetic acid in water
B: 0.1% v/v solution of trifluoroacetic acid in acetonitrile
Gradient:

| Time (min.) | A % | B % |
|---|---|---|
| 0 | 97 | 3 |
| 1.5 | 0 | 100 |
| 1.9 | 0 | 100 |
| 2.0 | 97 | 3 |

System 6
Column: 30 mm×4.6 mm ID, 3.5 μm Sunfire $C_{18}$ column
Flow Rate: 3 ml/min.
Temp.: 30° C.
UV Detection Range: 210 to 350 nm
Mass spectrum: Recorded on a mass spectrometer using alternative-scan positive and negative mode electrospray ionisation.
Solvents: A: 0.1% v/v solution of trifluoroacetic acid in water
B: 0.1% v/v solution of trifluoroacetic acid in acetonitrile
Gradient:

| Time (min.) | A % | B % |
|---|---|---|
| 0 | 97 | 3 |
| 0.1 | 97 | 3 |
| 4.2 | 0 | 100 |
| 4.8 | 0 | 100 |
| 4.9 | 97 | 3 |
| 5.0 | 97 | 3 |

System 7
Column: 50 mm×2.1 mm ID, 1.7 μm Acquity UPLC BEH $C_{18}$
Flow Rate: 1 ml/min.
Temp.: 40° C.
UV Detection Range: 220 to 350 nm
Mass spectrum: Recorded on a mass spectrometer using alternative-scan positive and negative mode electrospray ionisation.
Solvents: A: 10 mM ammonium bicarbonate in water adjusted to pH10 with ammonia solution
B: Acetonitrile
Gradient:

| Time (min.) | A % | B % |
|---|---|---|
| 0 | 99 | 1 |
| 1.5 | 3 | 97 |
| 1.9 | 3 | 97 |
| 2.0 | 0 | 100 |

System 8
Column: 50 mm×4.6 mm ID, 3.5 μm XBridge $C_{18}$ column
Flow Rate: 3 ml/min.
Temp.: 30° C.
UV Detection Range: 210 to 350 nm
Mass spectrum: Recorded on a mass spectrometer using alternative-scan positive and negative mode electrospray ionisation.
Solvents: A: 10 mM ammonium bicarbonate in water adjusted to pH10 with ammonia solution
B: Acetonitrile
Gradient:

| Time (min.) | A % | B % |
|---|---|---|
| 0 | 99 | 1 |
| 0.1 | 99 | 1 |
| 4.0 | 3 | 97 |
| 5.0 | 3 | 97 |

ABBREVIATIONS

The following list provides definitions of certain abbreviations as used herein. It will be appreciated that the list is not exhaustive, but the meaning of those abbreviations not herein below defined will be readily apparent to those skilled in the art.
Ac (acetyl);
Bu (butyl);
nBu (n-butyl);
tert-Bu (t-butyl);
DCM (dichloromethane);
DIPEA (N,N-Diisopropylethylamine);
DMF (N,N-dimethylformamide);
DMSO (dimethylsulfoxide);
Et (ethyl);
EtOAc (ethyl acetate);
g (grams);
h (hours)-

HATU (2-(7-aza-1H-benzotriazole-1-yl)-1,1,3,3-tetramethyluronium hexafluorophosphate)
HCl (Hydrochloric acid)
Hz (Hertz);
L (liters);
LCMS (liquid chromatography-mass spectrometry)
LDA (lithium diisopropylamide);
M (molar);
MDAP (mass directed autopreparative HPLC);
Me (methyl);
MeOH (methanol);
mg (milligrams);
MHz (megahertz);
min (minutes);
ml (milliliters); μl (microliters);
mM (millimolar);
mmol (millimoles);
mol (moles);
NBS (N-Bromosuccinimide)
PFA (perfluoroalkoxy)
Ph (phenyl);
$^i$Pr (isopropyl);
Rf (retention factor)
Si (Silica)
SPE (solid phase extraction);
TBTU (O-(benzotriazol-1-yl)-N,N,N',N'-tetramethyluronium tetrafluoroborate);
TEA (triethylamine);
TFA (trifluoroacetic acid);
THF (tetrahydrofuran);
TLC (thin layer chromatography);
TMS (trimethylsilyl);

All references to ether are to diethyl ether and brine refers to a saturated aqueous solution of NaCl.

The names of the above mentioned Examples have been obtained using the compound naming programme "ACD Name Pro 6.02".

Intermediate 1: 1H-Pyrazol-4-amine

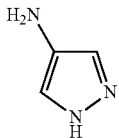

4-Nitro-1H-pyrazole (Manchester organics; 1.13 g, 9.99 mmol) was dissolved in ethanol (50 ml). This solution was added carefully to 10% palladium on carbon (Aldrich; 102 mg) under a nitrogen atmosphere. The atmosphere was exchanged to hydrogen, and the mixture was stirred vigorously at room temperature under a hydrogen atmosphere. After 45 min, ca. 700 ml of hydrogen had been taken up, and no further hydrogen was taken up over the next 30 min. Stirring was stopped and the atmosphere was exchanged to nitrogen. The solution was filtered through cellite (10 g cartridge) and washed with further ethanol (150 ml). Relevant fractions (as verified by TLC) were combined and concentrated in vacuo to give a red oil. Trituration with DCM gave the title compound (815 mg) as a red solid; $^1$H NMR (MeOH-$d_4$, 400 MHz) δ (ppm) 7.20 (2H, s).

Intermediate 2:
2,6-Difluoro-N-1H-pyrazol-4-ylbenzamide

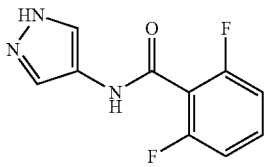

1H-Pyrazol-4-amine (for a preparation see intermediate 1; 0.54 g, 6.5 mmol) was dissolved in acetonitrile (25 ml) with triethylamine (1.81 ml, 13.0 mmol) to give a red-purple suspension which was cooled in an ice-water bath. To the suspension was added a solution of 2,6-difluorobenzoyl chloride (Aldrich; 0.817 ml, 6.5 mmol) in acetonitrile (25 ml) dropwise over 15 min. The mixture was stirred cold under nitrogen. The reaction was stirred and allowed to warm slowly towards room temperature over 2 h, then at room temperature for 30 min. The reaction mixture was partitioned between EtOAc and water (~100 ml each). The aqueous phase was extracted with further EtOAc (2×50 ml). The combined organic extracts were dried (MgSO$_4$) and concentrated in vacuo. The residue (1.41 g) was purified on silica (50 g) using 0-100% EtOAc-cyclohexane then 0-20% methanol-EtOAc. Relevant fractions were concentrated in vacuo to give some pure product (0.925 g) and some less pure material (0.50 g). The latter material was re-purified on silica (20 g) using EtOAc to give further pure product (0.366 g). The two batches of pure product were combined to give the title compound (1.28 g) as a pale cream solid; LCMS (System 1): MH$^+$=224, $t_{RET}$=2.08 min.

Intermediate 3: [2-(Butyloxy)phenyl]methanol

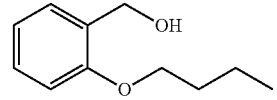

A solution of 2-(hydroxymethyl)phenol (Aldrich; 1.24 g, 10 mmol) and 1-bromobutane (Acros; 1.18 ml, 11 mmol) in ethanol (5 ml) (total volume approximately 7 ml) was mixed in a flow reactor (Vapourtec R4, 30 ml PFA tubing, 110° C.) with a solution of aqueous NaOH (2 N, 5 ml, 10 mmol) in water (2 ml). The reagents were each pumped at 0.5 ml/min), giving a reaction time of 30 minutes. After the 30 ml reactor, the solution passed through a second "cooling" reactor (5 ml) at 50° C. At the reactor output, a 250 psi back pressure regulator was used. After all starting solutions had been consumed, the system was purged with an additional 70 ml solvent (1:1, ethanol:water). The collected material was concentrated in vacuo. The residue was partitioned between water and EtOAc, and treated with saturated aqueous sodium bicarbonate solution. The aqueous phase was further extracted with EtOAc, and the combined organic extracts were dried (hydrophobic frit) and concentrated in vacuo. The residue was purified on silica (100 g) using 0-100% ethyl acetate-cyclohexane. The appropriate fractions were combined and concentrated in vacuo to give the title compound (1.4 g); LCMS (System 4): MNH$_4^+$=198, $t_{RET}$=2.51 min.

Intermediate 4:
1-(Bromomethyl)-2-(butyloxy)benzene

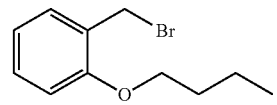

A solution of 2-(butyloxy)phenyl]methanol (for a preparation see intermediate 3; 6 g, 33.3 mmol) in DCM (30 ml) (total solution volume 34 ml) was mixed in a flow reactor (Vapourtec R4, 35 ml PFA tubing reactor, maintained at 25° C.) with a solution of phosphorus tribromide in DCM (Aldrich; 1 M, 33.6 ml, 33.6 mmol). The solutions were each pumped at 0.583 ml/min), giving a reaction time of 30 min. The output was collected into a stirred flask of water, which was subsequently treated with aqueous sodium bicarbonate (100 ml). The aqueous layer was extracted with DCM (×2), and the combined organic extracts were dried (hydrophobic frit) and concentrated in vacuo to give the title compound (6.8 g) as an opaque yellow oil; $^1$H NMR (DMSO-$d_6$, 400 MHz) δ (ppm) 7.38 (1H, dd, J 7.5, 2 Hz), 7.29 (1H, ddd, J 9, 7.5, 2 Hz), 7.00 (1H, d, J=9 Hz), 6.90 (1H, td, J 7.5, 1 Hz), 4.63 (2H, s), 4.03 (2H, t, J=6.5 Hz), 1.78-1.66 (2H, m), 1.56-1.44 (2H, m), 0.94 (3H, t, J=7.5 Hz).

Intermediate 5: 5-Chloro-2-(hydroxymethyl)phenol

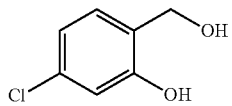

To a solution of 4-chloro-2-hydroxybenzoic acid (Aldrich; 2.0 g, 11.6 mmol) in THF (50 ml) was added dropwise 1 M borane in THF (20.9 ml, 20.9 mmol). The suspension was allowed to stir for 30 min at ambient temperature. The mixture was refluxed at 80° C. for 2.5 h. The solvent was removed in vacuo. The residue was loaded in dichloromethane and purified on silica (100 g) using 0-100% ethyl acetate/cyclohexane. The appropriate fractions were combined and evaporated in vacuo to give the title compound (1.51 g) as a white solid; LCMS (System 1): (M-H)$^-$=157, $t_{RET}$=2.44 min.

Intermediate 6: {4-Chloro-2-[(phenylmethyl)oxy]phenyl}methanol

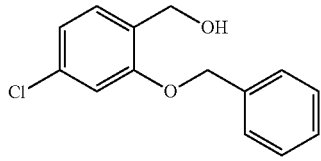 [SMILES: OCc1ccc(Cl)cc1OCc1ccccc1]

To a solution of 5-chloro-2-(hydroxymethyl)phenol (for a preparation see intermediate 5; 1.51 g, 9.54 mmol) in ethanol (20 ml), was added sodium hydroxide (5.25 ml, 10.5 mmol). To the mixture was added a solution of benzyl bromide (Aldrich; 1.14 ml, 9.54 mmol) in ethanol (30 ml) dropwise. The reaction was stirred under nitrogen overnight at ambient temperature. The solvent was removed in vacuo to leave an aqueous suspension. The suspension was diluted with water (50 ml) and dichloromethane (40 ml). The phases were separated and the aqueous phase extracted with dichloromethane (30 ml). The combined organic extracts were washed with saturated aqueous sodium hydrogen carbonate (20 ml) and the solvent removed in vacuo to leave a white solid (1.52 g). The residue was loaded in dichloromethane and purified on silica (100 g) using 0-50% ethyl acetate-cyclohexane. The appropriate fractions were combined and evaporated in vacuo to give the title compound (1.32 g) as a white solid; LCMS (System 2): (M-H)$^-$=247, $t_{RET}$=1.17 min.

Intermediate 7: 1-(Bromomethyl)-2-(phenylmethyl)benzene

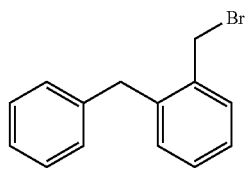 [SMILES: BrCc1ccccc1Cc1ccccc1]

2-(Phenylmethyl)phenyl]methanol (Acros; 393 mg, 1.98 mmol) was dissolved in DCM (5 ml) and cooled to −10° C. (external acetone/CO$_2$ bath) under nitrogen. A solution of phosphorous tribromide (Aldrich; 190 μl, 2.02 mmol) in DCM (5 ml) was added dropwise to the stirred solution under nitrogen. The reaction mixture was stirred under nitrogen and allowed to warm slowly to ambient temperature overnight. The reaction mixture was re-cooled in an ice-water bath and quenched by the addition of saturated aqueous sodium hydrogen carbonate solution (5 ml) with stirring. The layers were separated and the aqueous layer was washed with DCM (2×10 ml). The combined DCM extracts were dried (MgSO$_4$) and concentrated to give the title compound as an oil, which became a pale pink crystalline solid on standing (466 mg); LCMS (System 4): $t_{RET}$=3.99 min, no MH$^+$ detected.

Intermediate 8: 1-({5-Chloro-2-[(phenylmethyl)oxy]phenyl}methyl)-4-nitro-1H-pyrazole

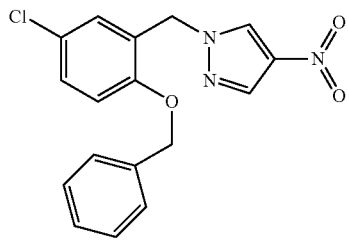 [SMILES: O=[N+]([O-])c1cnn(Cc2cc(Cl)ccc2OCc2ccccc2)c1]

To a solution of 4-nitropyrazole (Manchester organics; 0.503 g, 4.45 mmol) in DMF (10 ml) was added potassium carbonate (1.24 g, 9.0 mmol), sodium iodide (24 mg, 0.160 mmol) and then 2-(bromomethyl)-4-chloro-1-[(phenylmethyl)oxy]benzene (synthesised according to WO2006066968; 1.23 g, 3.95 mmol). The reaction was stirred at ambient temperature overnight. A further amount of 2-(bromomethyl)-4-chloro-1-[(phenylmethyl)oxy]benzene (156 mg) was added and the reaction was stirred at ambient temperature for a further 30 min. The reaction mixture was concentrated in vacuo and treated with water (60 ml). The aqueous solution was extracted with ethyl acetate (3×60 ml). The combined organic layers were dried (MgSO$_4$) and concentrated in vacuo. The sample was loaded in dichloromethane and purified on silica (50 g) using 0-100% ethyl acetate-cyclohexane. The appropriate fractions were combined and evaporated in vacuo to give the title compound (1.17 g) as a white solid; LCMS (System 1): MH$^+$=344, $t_{RET}$=3.58 min.

Intermediate 9: 1-({5-Chloro-2-[(phenylmethyl)oxy] phenyl}methyl)-1H-pyrazol-4-amine

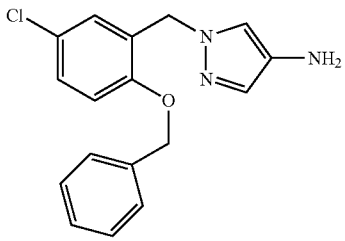 [SMILES: Nc1cnn(Cc2cc(Cl)ccc2OCc2ccccc2)c1]

To a solution of 1-({5-chloro-2-[(phenylmethyl)oxy] phenyl}methyl)-4-nitro-1H-pyrazole (for a preparation see intermediate 8; 476 mg, 1.39 mmol) in ethanol (15 ml) was added stannous chloride (hydrated) (1.59 g, 7.03 mmol) and the reaction stirred at 85° C. overnight, under nitrogen. The reaction mixture was applied to a 20 g SCX-2 cartridge (pre-washed with MeOH) and the cartridge washed with methanol (6 column volumes). The product was eluted with 10% $NH_3$ (aqueous) in MeOH (4 column volumes). The combined basic fractions were concentrated in vacuo. The residue was loaded in dichloromethane and purified on silica (50 g) using 0-100% ethyl acetate-cyclohexane. The appropriate fractions were combined and evaporated in vacuo to give the title compound (191 mg) as a red gum; LCMS (System 1): $MH^+$=314, $t_{RET}$=2.69 min.

Intermediate 10: 1-{[2-Fluoro-6-(trifluoromethyl) phenyl]methyl}-4-nitro-1H-pyrazole

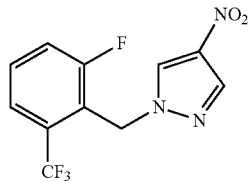 [SMILES: O=[N+]([O-])c1cnn(Cc2c(F)cccc2C(F)(F)F)c1]

4-Nitropyrazole (Aldrich; 4.974 g, 44.0 mmol) was dissolved in DMF (100 ml) and potassium carbonate (9.12 g, 66.0 mmol) was added. The reaction mixture was allowed to stir at ambient temperature under nitrogen for approximately 5 minutes. 2-(Bromomethyl)-1-fluoro-3-(trifluoromethyl) benzene (Aldrich; 11.31 g, 44.0 mmol) in DMF (25 ml) was then added over a period of approximately 5 minutes and the reaction was left to stir overnight.

The reaction mixture was partitioned between ethyl acetate (500 ml) and water (500 ml). The organic layer was washed with water (2×250 ml) and dried over sodium sulfate. The solvent was then evaporated under vacuum to give the title compound (12.52 g) as an oil; LCMS (System 3): $MNH_4^+$=307, $t_{RET}$=1.06 min.

Intermediate 11: 1-{[2-Fluoro-6-(trifluoromethyl) phenyl]methyl}-1H-pyrazol-4-amine hydrochloride

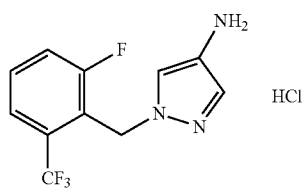 [SMILES: Nc1cnn(Cc2c(F)cccc2C(F)(F)F)c1 ; Cl]

1-{[2-Fluoro-6-(trifluoromethyl)phenyl]methyl}-4-nitro-1H-pyrazole (for a preparation see intermediate 10; 12.52 g, 43.3 mmol) was dissolved in ethanol (300 ml) and added to palladium on carbon (Aldrich, 10% wet Degussa type E101 NE/W; 1.25 g). The vessel was purged with nitrogen and then charged with hydrogen and left to stir overnight.

After 17 h stirring at ambient temperature under a hydrogen atmosphere, the vessel was charged again with hydrogen and stirring resumed for 3.5 h but no further hydrogen was taken-up by the reaction. The reaction was then purged with nitrogen and the catalyst removed by filtration through a pad of celite. The solvent was then removed under vacuum to give a crude product (11.76 g). The crude product was dissolved in diethyl ether (450 ml) and 1.0 M hydrochloric acid in diethyl ether (50 ml) was added. The resulting suspension was stirred vigorously for 5 minutes then the precipitate was collected by filtration and washed with ether (3×50 ml). The product was dried under vacuum at 60° C. overnight to give the title compound (12.14 g) as an off-white solid; LCMS (System 3): $MH^+$=260, $t_{RET}$=0.56 min.

Intermediate 12: Chloromethyl bis(1,1-dimethylethyl)phosphate

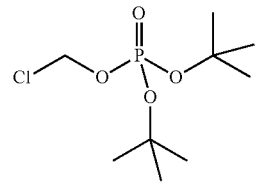

Potassium bicarbonate (Sigma; 1.55 g, 15.48 mmol) and potassium permanganate (VWR; 2.85 g, 18.03 mmol) were dissolved in water (120 ml). The solution was stirred vigorously at ambient temperature for about 15 minutes to ensure that all of the reagents had dissolved. The reaction mixture was then cooled to –0° C. (internal temperature) and di-tert-butyl phosphite (Alfa Aesar; 4.8 g, 24.72 mmol) was added in roughly 1 g portions every 10 minutes. Throughout the addition the temperature was maintained between –1 and +3° C. Once the addition was complete the reaction was allowed to warm slowly back to ambient temperature.

After stirring overnight the thick brown solution was filtered through a pad of celite (10 g) and washed with water (25 ml). The pink solution was then concentrated under vacuum to about 65 ml. The solution was filtered again and washed with water (10 ml).

Potassium bicarbonate (Sigma; 12.38 g, 124 mmol) and tetrabutylammonium hydrogen sulfate (Fluka; 0.840 g, 2.47 mmol) were added to the pale pink aqueous solution and the mixture was stirred for about 5 minutes at ambient temperature to ensure that all of the reagents had dissolved. DCM (75 ml) was then added and the reaction was left to stir for about an hour before cooling to 5° C. A solution of chloromethyl chlorosulfate (Fluorochem; 5.10 g, 30.9 mmol) in DCM (50 ml) was then added via a syringe pump over a period of 3 hours whilst maintaining the internal temperature at 5° C. After the addition was complete the reaction was allowed to warm slowly to ambient temperature and left to stir for 68 hours. The phases were then separated and the bottom organic phase was washed with water (3×250 ml). The DCM phase was passed through a hydrophobic frit and the stock solution of the title compound was transferred to a refrigerator. The solution molarity was determined to be 0.13 M and hence the yield of the title compound was 4.3 g.

Intermediate 13: [[(2,6-Difluorophenyl)carbonyl](1-{[2-fluoro-6-(trifluoromethyl)phenyl]methyl}-1H-pyrazol-4-yl)amino]methyl bis(1,1-dimethylethyl) phosphate

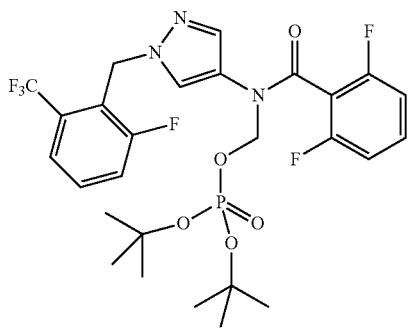 [SMILES: CC(C)(C)OP(=O)(OCN(C(=O)c1c(F)cccc1F)c1cnn(Cc2c(F)cccc2C(F)(F)F)c1)OC(C)(C)C]

2,6-Difluoro-N-(1-{[2-fluoro-6-(trifluoromethyl)phenyl]methyl}-1H-pyrazol-4-yl)benzamide (for a preparation see example 6; 110 mg, 0.275 mmol) and potassium hydroxide (21.6 mg, 0.386 mmol, 1.4 eq.) were weighed into a vial and then a solution of chloromethyl bis(1,1-dimethylethyl)phosphate (for a preparation see Intermediate 12; 57 mg, 0.220 mmol, 0.8 eq.) in DMF (1 ml) was added. (Note that a DCM stock solution of intermediate 12 was carefully evaporated (without heating) immediately before use in this step: 1.6 ml provided 57 mg). The vial was sealed and the solution was stirred vigorously at ambient temperature.

After 6 h 30 min further quantities of potassium hydroxide (3.1 mg, 0.055 mmol, 0.2 eq.) and chloromethyl bis(1,1-dimethylethyl)phosphate (57 mg, 0.220 mmol, 0.8 eq.) were added and the reaction was left to stir overnight at ambient temperature.

After approximately 22 h the reaction mixture was filtered through a plug of cotton wool and was diluted with 1:1 DMSO:MeOH to a total volume of 2 ml. The sample was then purified (2×1 ml injections) by MDAP (Method E) on Xbridge column using acetonitrile-water with an ammonium carbonate modifier.

The product containing fractions were combined and partitioned between tert-butyl methyl ether (TBME) (50 ml) and water (100 ml) and the water layer was extracted again with TBME (50 ml). The combined TBME extracts were dried ($Na_2SO_4$) and evaporated to give the title product (90.4 mg) as an oil; LCMS (System 3): $MH^+=622$, $t_{RET}=1.26$ min.

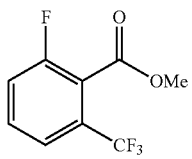 [SMILES: COC(=O)c1c(F)cccc1C(F)(F)F]

Intermediate 14: Methyl 2-fluoro-6-(trifluoromethyl)benzoate

2-Fluoro-6-(trifluoromethyl)benzoyl chloride (Sigma-Aldrich; 950 mg, 4.19 mmol) was added drop-wise to dry methanol (5 mL) under nitrogen. After 18 hours LCMS indicated that no starting material remained. The reaction solution was partitioned between DCM (~50 mL) and saturated aqueous sodium bicarbonate. The aqueous layer was extracted with further DCM and the combined DCM extracts were dried (sodium sulfate) and evaporated to give the title product as a colourless liquid (786 mg). This material was used in the next step without further purification. LCMS (System 3): $t_{RET}=1.05$ min.

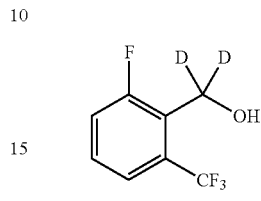

Intermediate 15: (2-Fluoro-6-(trifluoromethyl)phenyl)-$d_2$-methanol

Lithium aluminium deuteride (1 M solution in THF, 7.37 mL, 7.37 mmol) was transferred to a RBF under nitrogen. A solution of methyl 2-fluoro-6-(trifluoromethyl)benzoate (for a preparation see intermediate 14; 780 mg, 3.51 mmol) in tetrahydrofuran (5 mL) was then added drop-wise over a period of approximately 10 minutes. After 1 hour the reaction was cooled in an ice bath and saturated aqueous sodium sulfate was added drop-wise until gas evolution had ceased. Further sodium sulfate solution was added (~25 mL total) and the reaction was left to stir at ambient temperature for 10 minutes. The reaction mixture was then extracted with TBME (2×50 mL), dried over sodium sulfate, and evaporated to give a crude product. The sample was loaded in cyclohexane and purified on silica (50 g) using a 0-50% ethyl acetate-cyclohexane gradient over 40 mins. The appropriate fractions were combined and evaporated in vacuo to give the title product (197 mg) as a colourless oil. LCMS (System 3): $t_{RET}=0.79$ min.

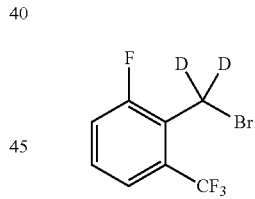

Intermediate 16: 2-(Bromo-$d_2$-methyl)-1-fluoro-3-(trifluoromethyl)benzene (2-Fluoro-6-(trifluoromethyl)phenyl)-$d_2$-methanol (for a preparation see intermediate 15; 192 mg, 0.979 mmol) was dissolved in dichloromethane (2 mL). Phosphorus tribromide (115 μL, 1.219 mmol) was added in one portion and the reaction was stirred at ambient temperature. After approximately 75 min the reaction had almost reached completion by LCMS. The reaction was quenched with water (1 mL), followed by saturated aqueous sodium bicarbonate until the pH of the aqueous phase was >8. The reaction mixture was diluted with more DCM and water and the layers were separated. The aqueous layer was extracted with further DCM and the combined extracts were dried (sodium sulfate) and evaporated to give the title product (79 mg) which was used directly in the next step without further purification. LCMS (System 3): $t_{RET}=1.20$ min.

Example 1

2,6-Difluoro-N-(1-{([2-(phenyloxy)phenyl]methyl}-1H-pyrazol-4-yl)benzamide

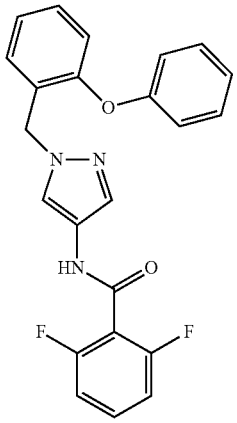 [SMILES: O=C(Nc1cnn(Cc2ccccc2Oc2ccccc2)c1)c1c(F)cccc1F]

A solution of 2,6-difluoro-N-1H-pyrazol-4-ylbenzamide (for a preparation see intermediate 2; 22 mg, 0.1 mmol) in DMF (0.4 ml) was treated with potassium tert-butoxide (11 mg, 0.1 mmol) and allowed to stand at room temperature for 10 min. A solution of 1-(bromomethyl)-2-phenoxybenzene (Maybridge; 26 mg, 0.1 mmol) in acetonitrile (0.2 ml) was finally added and the solution left to stand for 16 h at room temperature. The solvent was removed and then the crude mixture was dissolved in a 1:1 mixture of DMSO:methanol (0.6 ml) and the solution purified by MDAP on Sunfire C18 (Method D). The appropriate fraction was concentrated in vacuo to give the title compound (2.6 mg); LCMS (System 1): $MH^+$=406, $t_{RET}$=3.46 min.

Similarly prepared were:

| Example | Structure | Name | LCMS $t_{RET}$/min | $MH^+$ |
|---|---|---|---|---|
| 2 | 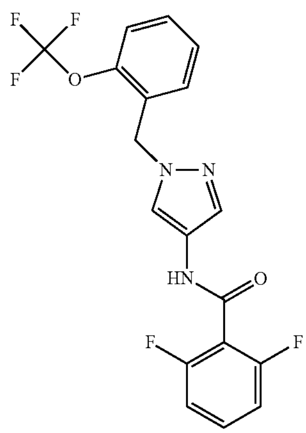 [SMILES: O=C(Nc1cnn(Cc2ccccc2OC(F)(F)F)c1)c1c(F)cccc1F] | 2,6-Difluoro-N-[1-({2-[(trifluoromethyl)oxy]phenyl}methyl)-1H-pyrazol-4-yl]benzamide | 1.10 (System 3) | 398 |
| 3 | 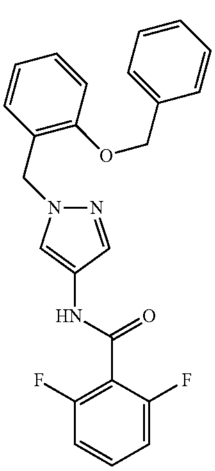 [SMILES: O=C(Nc1cnn(Cc2ccccc2OCc2ccccc2)c1)c1c(F)cccc1F] | 2,6-Difluoro-N-[1-({2-[(phenylmethyl)oxy]phenyl}methyl)-1H-pyrazol-4-yl]benzamide | 1.17 (System 3) | 420 |

-continued

| Example | Structure | Name | LCMS t$_{RET}$/min | MH+ |
|---|---|---|---|---|
| 4 | 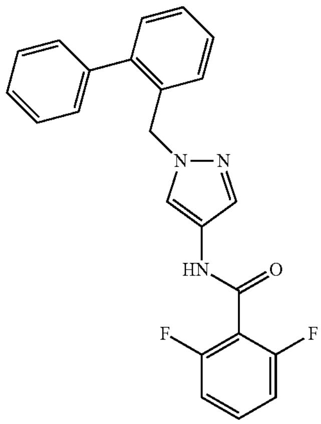 [SMILES: O=C(Nc1cnn(Cc2ccccc2-c2ccccc2)c1)c1c(F)cccc1F] | N-[1-(2-Biphenylylmethyl)-1H-pyrazol-4-yl]-2,6-difluorobenzamide | 3.45 (System 1) | 390 |
| 5 | 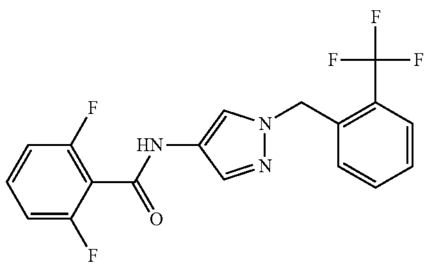 [SMILES: O=C(Nc1cnn(Cc2ccccc2C(F)(F)F)c1)c1c(F)cccc1F] | 2,6-Difluoro-N-(1-{[2-(trifluoromethyl)phenyl]methyl}-1H-pyrazol-4-yl)benzamide | 1.14 (System 3) | 382 |
| 6 | 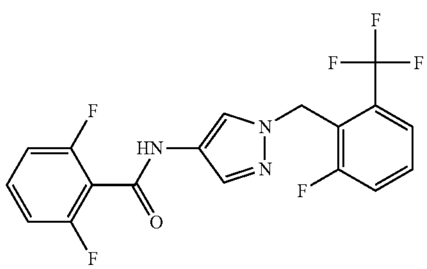 [SMILES: O=C(Nc1cnn(Cc2c(F)cccc2C(F)(F)F)c1)c1c(F)cccc1F] | 2,6-Difluoro-N-(1-{[2-fluoro-6-(trifluoromethyl)phenyl]methyl}-1H-pyrazol-4-yl)benzamide | 3.21 (System 1) | 400 |
| 7 | 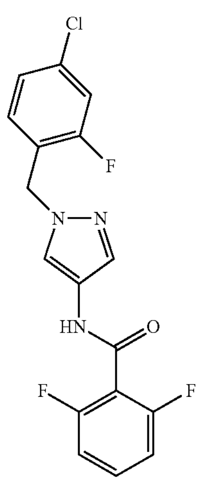 [SMILES: O=C(Nc1cnn(Cc2ccc(Cl)cc2F)c1)c1c(F)cccc1F] | N-{(1-[(4-Chloro-2-fluorophenyl)methyl]-1H-pyrazol-4-yl}-2,6-difluorobenzamide | 1.11 (System 3) | 366 |

| Example | Structure | Name | LCMS $t_{RET}$/min | MH+ |
|---|---|---|---|---|
| 8 | 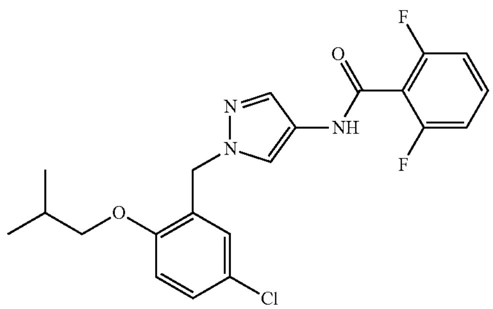 [SMILES: CC(C)COc1ccc(Cl)cc1Cn1cc(NC(=O)c2c(F)cccc2F)cn1] | N-[1-({5-Chloro-2-[(2-methylpropyl)oxy]phenyl}methyl)-1H-pyrazol-4-yl]-2,6-difluorobenzamide | 3.66 (System 1) | 420 |
| 9 | 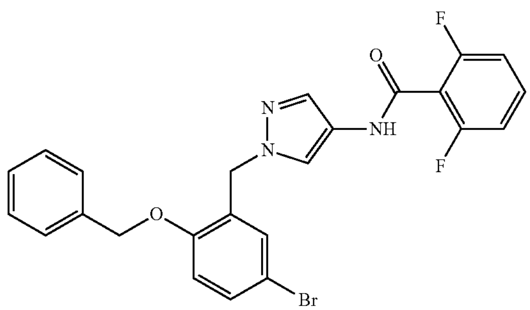 [SMILES: O=C(Nc1cnn(Cc2cc(Br)ccc2OCc2ccccc2)c1)c1c(F)cccc1F] | N-[1-({5-Bromo-2-[(phenylmethyl)oxy]phenyl}methyl)-1H-pyrazol-4-yl]-2,6-difluorobenzamide | 3.67 (System 1) | 498 |
| 10 | 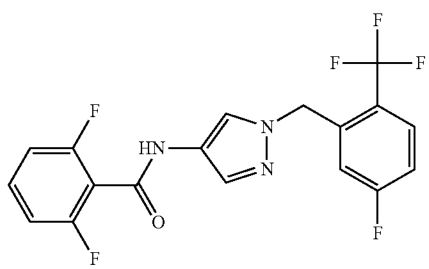 [SMILES: O=C(Nc1cnn(Cc2cc(F)ccc2C(F)(F)F)c1)c1c(F)cccc1F] | 2,6-Difluoro-N-(1-{[5-fluoro-2-(trifluoromethyl)phenyl]methyl}-1H-pyrazol-4-yl)benzamide | 3.33 (System 1) | 400 |
| 11 | 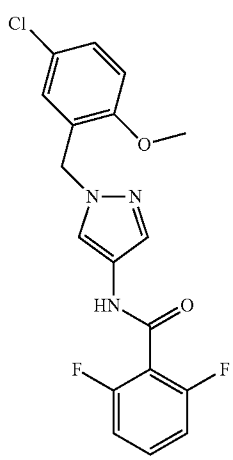 [SMILES: COc1ccc(Cl)cc1Cn1cc(NC(=O)c2c(F)cccc2F)cn1] | N-(1-{[5-Chloro-2-(methyloxy)phenyl]methyl}-1H-pyrazol-4-yl)-2,6-difluorobenzamide | 3.27 (System 1) | 378 |
| 29 | | 2,6-difluoro-N-(1-(2-methoxybenzyl)-1H-pyrazol-4-yl)benzamide | | |

Example 6 can also be prepared according to the following procedure:

Example 6

2,6-Difluoro-N-(1-{([2-fluoro-6-(trifluoromethyl) phenyl]methyl}-1H-pyrazol-4-yl)benzamide 1-{[2-Fluoro-6-(trifluoromethyl)phenyl]methyl}-1H-pyrazol-4-amine hydrochloride (for a preparation see intermediate 11; 12.14 g, 41.1 mmol) was suspended in DCM (350 ml) and stirred vigorously under nitrogen. DIPEA (17.9 ml, 103 mmol) was added and once all of the material had dissolved 2,6-difluorobenzoyl chloride (5.16 ml, 41.1 mmol) was added. After 1 h the reaction solution was washed with 2 M aqueous HCl (200 ml), water (200 ml) and finally saturated sodium bicarbonate solution (200 ml). The DCM solution was then dried over sodium sulfate and evaporated to give a crude product. The product was loaded in ethyl acetate and purified on silica (750 g) using a 5-60% ethyl acetate-cyclohexane gradient over 8 column volumes. The appropriate fractions were combined and evaporated in vacuo to give a product (15.07 g) as a pale purple solid. The product was then triturated with chloroform and the resulting white product was collected by filtration. The product was washed with diethyl ether and dried under vacuum at 60° C. The solution from the trituration step yielded further crops of product on standing and these were also washed with diethyl ether and combined with the first crop to give the title compound (12.34 g) as a white solid; LCMS (System 3): MH$^+$=400, $t_{RET}$=1.04 min; $^1$H NMR (DMSO-d$_6$, 600 MHz): δ (ppm) 10.83 (1H, s), 8.03 (1H, s), 7.67-7.72 (2H, m), 7.62-7.67 (1H, m), 7.57 (1H, tt, J 8.5, 6.5 Hz), 7.46 (1H, s), 7.22 (2H, t, J=8.0 Hz), 5.48 (2H, s).

Example 12

N-(1-{[2-(Butyloxy)phenyl]methyl}-1H-pyrazol-4-yl)-2,6-difluorobenzamide

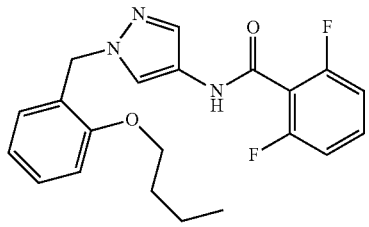 [SMILES: CCCCOc1ccccc1Cn1cc(NC(=O)c2c(F)cccc2F)cn1]

2,6-Difluoro-N-1H-pyrazol-4-ylbenzamide (for a preparation see intermediate 2, 45 mg, 0.20 mmol), 1-(bromomethyl)-2-(butyloxy)benzene (for a preparation see intermediate 4, 56 mg, 0.23 mmol) and potassium carbonate (42 mg, 0.30 mmol) were weighed into a vial with a stirrer. DMF (0.5 ml) was added, the vial was capped and the mixture was stirred at ambient temperature for 26 h. The reaction mixture was filtered, washing with MeOH to give a total volume of 1 ml. This solution was purified by MDAP Sunfire C18 column (Method B) using acetonitrile-water with a formic acid modifier. The solvent was removed to give the title compound (25 mg) as a colourless gum; LCMS (System 4): MH$^+$=386, $t_{RET}$=3.02 min.

Example 13

2,6-Difluoro-N-[1-({2-[(phenyloxy)methyl] phenyl}methyl)-1H-pyrazol-4-yl]benzamide

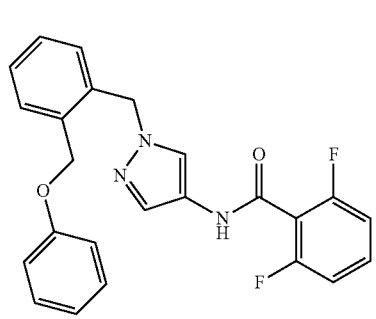 [SMILES: O=C(Nc1cnn(Cc2ccccc2COc2ccccc2)c1)c1c(F)cccc1F]

2,6-Difluoro-N-1H-pyrazol-4-ylbenzamide (for a preparation see intermediate 2, 45 mg, 0.20 mmol), potassium carbonate (42 mg, 0.30 mmol) and 1-(bromomethyl)-2-[(phenyloxy)methyl]benzene (Maybridge; 68 mg, 0.25 mmol) were weighed into a vial with a stirrer. DMF (1 ml) was added, the vial was capped and the mixture was stirred at ambient temperature for 17 h. The reaction mixture was filtered, washing with MeOH to give a total volume of 2 ml. This solution was purified by MDAP Sunfire C18 column (Method B) using acetonitrile-water with a formic acid modifier. The solvent was removed to give the title compound (37 mg) as a colourless gum; LCMS (System 4): MH$^+$=420, $t_{RET}$=3.05 min.

Example 14

N-[1-({4-Chloro-2-[(phenylmethyl)oxy] phenyl}methyl)-1H-pyrazol-4-yl]-2,6-difluorobenzamide

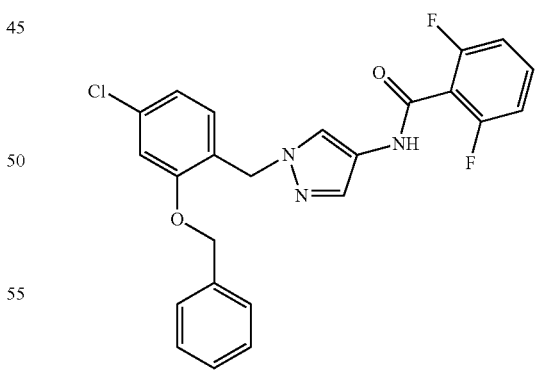

To a solution of {4-chloro-2-[(phenylmethyl)oxy] phenyl}methanol (for a preparation see intermediate 6) (0.501 g, 2.02 mmol) in DCM (10 ml) at −10 to −15° C., under nitrogen, was added a solution of phosphorus tribromide (0.190 ml, 2.02 mmol, Aldrich) in DCM (5 ml) dropwise. The solution was allowed to warm to ambient temperature and stirred for 4.5 h. To the reaction mixture in an ice-water bath was added dropwise saturated aqueous sodium hydrogen carbonate (5 ml). The mixture was diluted with water (45 ml) and dichloromethane (55 ml). The phases were separated and the aqueous phase washed with DCM (30 ml). The combined organic extracts were washed with water (10 ml). The organic extract was dried (MgSO$_4$), filtered and the solvent removed in vacuo to give 1-(bromomethyl)-4-chloro-2-[(phenylmethyl)oxy]benzene (0.505 g) as a colourless gum.

To 2,6-difluoro-N-1H-pyrazol-4-ylbenzamide (for a preparation see intermediate 2, 52 mg, 0.23 mmol) and potassium carbonate (65 mg, 0.47 mmol) was added a solution of 1-(bromomethyl)-4-chloro-2-[(phenylmethyl)oxy]benzene (74 mg, 0.27 mmol) in DMF (1 ml). The reaction was stirred overnight, under nitrogen and at ambient temperature. The suspension was filtered using a hydrophobic frit and the residue washed with methanol (1 ml). The filtrate was purified by MDAP (Method A) on Supelcosil ABZ+Plus column using acetonitrile-water with a formic acid modifier. The solvent was evaporated in vacuo to give the title compound (33 mg) as a white solid; LCMS (System 1): MH$^+$=454, $t_{RET}$=3.60 min.

Example 15

2,6-Difluoro-N-(1-{[2-(phenylmethyl)phenyl]methyl}-1H-pyrazol-4-yl)benzamide

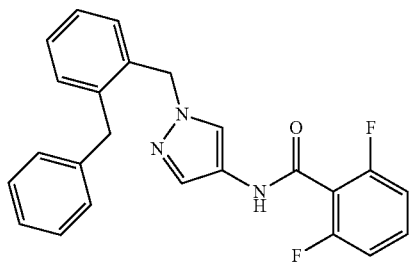 [SMILES: O=C(Nc1cnn(Cc2ccccc2Cc2ccccc2)c1)c1c(F)cccc1F]

2,6-Difluoro-N-1H-pyrazol-4-ylbenzamide (for a preparation see intermediate 2, 45 mg, 0.20 mmol), potassium carbonate (42 mg, 0.30 mmol) and 1-(bromomethyl)-2-(phenylmethyl)benzene (for a preparation see intermediate 7, 64 mg, 0.25 mmol) were weighed into a vial. DMF (1 ml) was added, the vial was capped and the mixture was stirred at ambient temperature overnight. The reaction was filtered through cotton wool, washing with MeOH to give a total volume of 2 ml. The mixture was purified by MDAP on the Sunfire column (Method D). The solvent was removed in vacuo to give the title compound (15 mg) as a colourless solid; LCMS (System 4): MH$^+$=404, $t_{RET}$=3.09 min.

Example 16

2,6-Dichloro-N-{1-[(2,4-dichlorophenyl)methyl]-1H-pyrazol-4-yl}benzamide

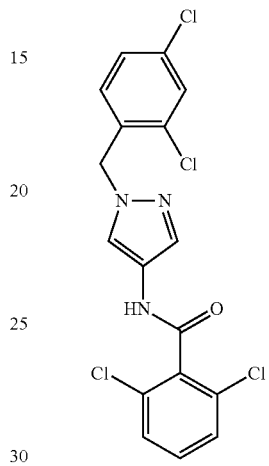

A solution of HATU (46 mg, 0.12 mmol) in DMF (200 μl) was added to 2,6-dichlorobenzoic acid (22 mg, 0.11 mmol, Avocado) followed by DIPEA (50 μl, 0.286 mmol) and left to stand for 5 min at ambient temperature. A solution of 1-[(2,4-dichlorophenyl)methyl]-1H-pyrazol-4-amine (Art Chem GmbH; 53 mg, 0.22 mmol) in DMF (200 μl) was then added and the solution left to stand for 16 h at ambient temperature. The solvent was removed using a Genevac. The sample was dissolved in 1:1 MeOH:DMSO (0.6 ml) and purified by MDAP on a standard C18 column (method D) using acetonitrile-water with a TFA modifier. The solvent was evaporated in vacuo using a Genevac to give the title compound (35 mg); LCMS (System 3): MH$^+$=414, $t_{RET}$=1.18 min.

Similarly prepared were:

| Example | Structure | Name | LCMS $t_{RET}$/min | MH$^+$ |
|---|---|---|---|---|
| 17 | 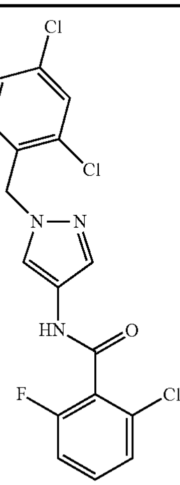 | 2-Chloro-N-{1-[(2,4-dichlorophenyl)methyl]-1H-pyrazol-4-yl}-6-fluorobenzamide | 1.15 (System 3) | 398 |

-continued
| Example | Structure | Name | LCMS t_RET/min | MH+ |
|---|---|---|---|---|
| 18 | 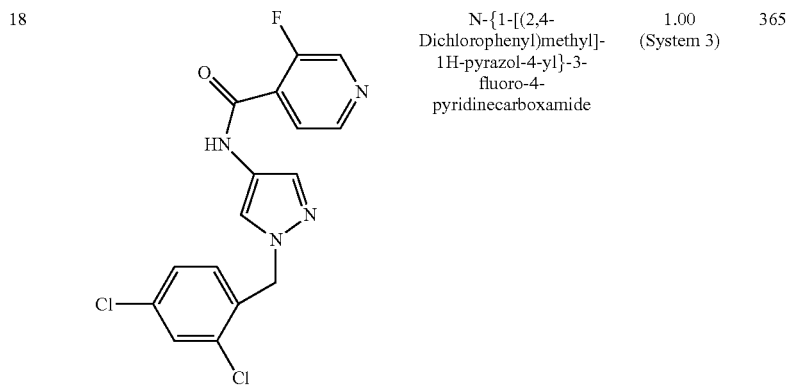 | N-{1-[(2,4-Dichlorophenyl)methyl]-1H-pyrazol-4-yl}-3-fluoro-4-pyridinecarboxamide | 1.00 (System 3) | 365 |
| 19 | 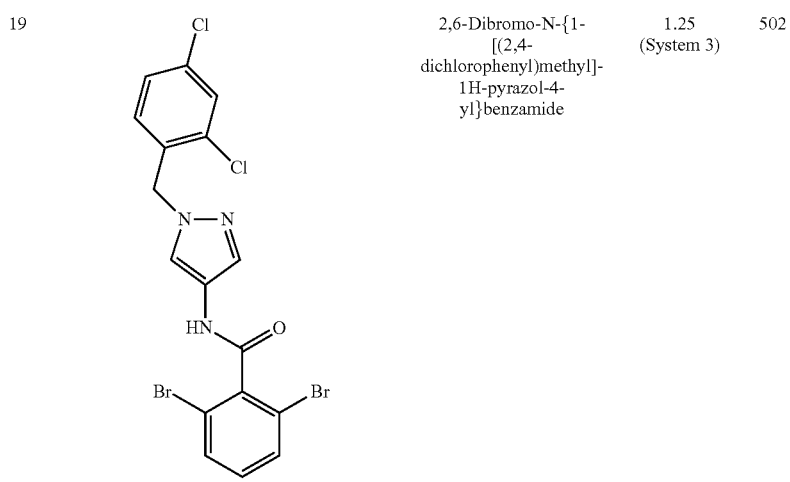 | 2,6-Dibromo-N-{1-[(2,4-dichlorophenyl)methyl]-1H-pyrazol-4-yl}benzamide | 1.25 (System 3) | 502 |
| 20 | 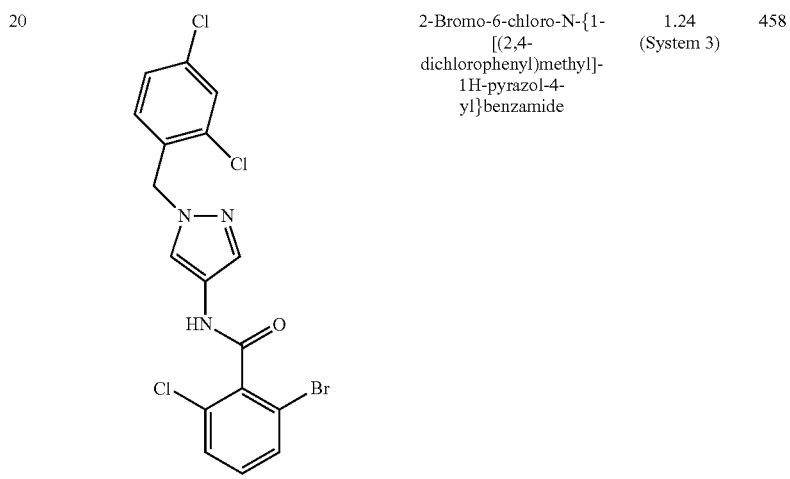 | 2-Bromo-6-chloro-N-{1-[(2,4-dichlorophenyl)methyl]-1H-pyrazol-4-yl}benzamide | 1.24 (System 3) | 458 |

| Example | Structure | Name | LCMS $t_{RET}$/min | MH⁺ |
|---|---|---|---|---|
| 21 | 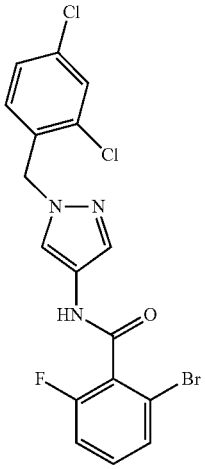 [SMILES: O=C(Nc1cnn(Cc2ccc(Cl)cc2Cl)c1)c1c(F)cccc1Br] | 2-Bromo-N-{1-[(2,4-dichlorophenyl)methyl]-1H-pyrazol-4-yl}-6-fluorobenzamide | 1.19 (System 3) | 442 |
| 22 | 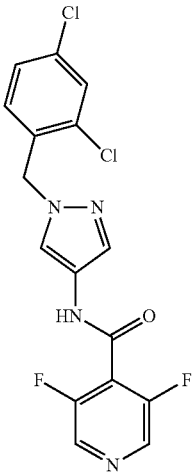 [SMILES: O=C(Nc1cnn(Cc2ccc(Cl)cc2Cl)c1)c1c(F)cncc1F] | N-{1-[(2,4-Dichlorophenyl)methyl]-1H-pyrazol-4-yl}-3,5-difluoro-4-pyridinecarboxamide | 1.07 (System 3) | 383 |
| 23 | 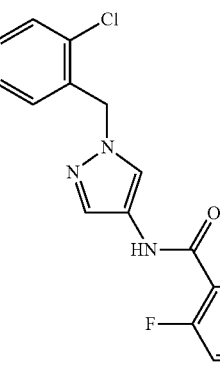 | N-{1-[(2,4-Dichlorophenyl)methyl]-1H-pyrazol-4-yl}-2,6-difluorobenzamide | 1.12 (System 3) | 382 |

-continued

| Example | Structure | Name | LCMS $t_{RET}$/min | MH+ |
|---|---|---|---|---|
| 24 | 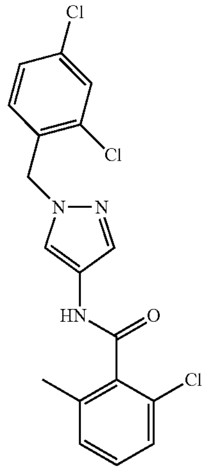 [SMILES: Cc1cccc(Cl)c1C(=O)Nc1cnn(Cc2ccc(Cl)cc2Cl)c1] | 2-Chloro-N-{1-[(2,4-dichlorophenyl)methyl]-1H-pyrazol-4-yl}-6-methylbenzamide | 1.20 (System 3) | 394 |
| 25 | 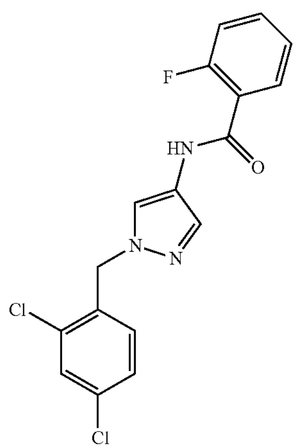 [SMILES: O=C(Nc1cnn(Cc2ccc(Cl)cc2Cl)c1)c1ccccc1F] | N-{1-[(2,4-Dichlorophenyl)methyl]-1H-pyrazol-4-yl}-2-fluorobenzamide | 1.14 (System 3) | 364 |

Example 26

2-Chloro-N-[1-({5-chloro-2-[(phenylmethyl)oxy]phenyl}methyl)-1H-pyrazol-4-yl]-6-fluorobenzamide

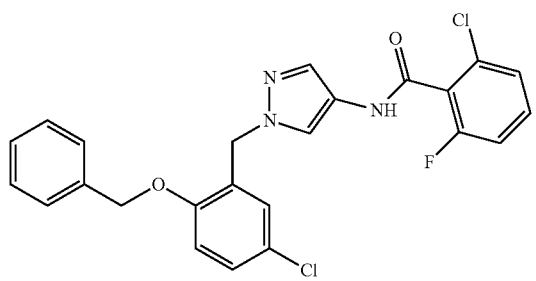 [SMILES: O=C(Nc1cnn(Cc2cc(Cl)ccc2OCc2ccccc2)c1)c1c(F)cccc1Cl]

The title compound was prepared in a similar fashion to the preparation of example 16, replacing 1-[(2,4-dichlorophenyl)methyl]-1H-pyrazol-4-amine with 1-({5-chloro-2-[(phenylmethyl)oxy]phenyl}methyl)-1H-pyrazol-4-amine (for a preparation see intermediate 9) and replacing 2,6-dichlorobenzoic acid with 2-chloro-6-fluorobenzoic acid (Aldrich); LCMS (System 3): MH+=470, $t_{RET}$=1.28 min.

Example 27

N-[1-({5-Chloro-2-[(phenylmethyl)oxy]phenyl}methyl)-1H-pyrazol-4-yl]-2,6-difluorobenzamide

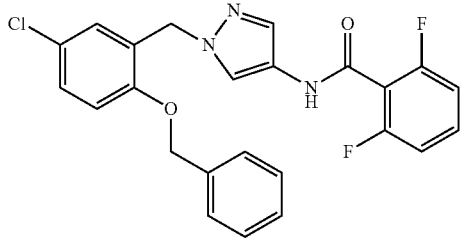 [SMILES: O=C(Nc1cnn(Cc2cc(Cl)ccc2OCc2ccccc2)c1)c1c(F)cccc1F]

2,6-Difluoro-N-1H-pyrazol-4-ylbenzamide (for a preparation see Intermediate 2; 86 mg, 0.385 mmol) was dissolved in DMF (2.5 ml), sodium iodide (21 mg, 0.140 mmol), potassium carbonate (169 mg, 1.22 mmol) and 2-(bromomethyl)-4-chloro-1-[(phenylmethyl)oxy]benzene (synthesised according to Bioorganic & Medicinal Chemistry Letters (2009), 19, 2599-2603; 121 mg, 0.388 mmol) were then added using further DMF (2.5 ml). The reaction was then stirred overnight. Further 2-(bromomethyl)-4-chloro-1-[(phenylmethyl)oxy]benzene (125 mg) was added and the reaction was stirred for 4 h. The reaction was concentrated in vacuo. The crude material was treated with water (50 ml) and the aqueous solution was extracted with ethyl acetate (3×50 ml). The combined organic extracts were dried (MgSO$_4$) and concentrated in vacuo. The sample was loaded in ethyl acetate and purified on silica (20 g) using 0-100% ethyl acetate-cyclohexane. The appropriate fractions were combined and evaporated in vacuo to give the title compound (70 mg) as a colourless gum; LCMS (System 1): MH$^+$=454, t$_{RET}$=3.59 min.

Example 28

[[(2,6-Difluorophenyl)carbonyl](1-{[2-fluoro-6-(trifluoromethyl)phenyl]methyl}-1H-pyrazol-4-yl)amino]methyl dihydrogen phosphate

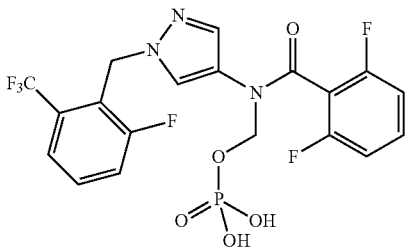 [SMILES: O=C(c1c(F)cccc1F)N(COP(=O)(O)O)c1cnn(Cc2c(F)cccc2C(F)(F)F)c1]

A pH 5 buffer solution was prepared by adding 0.2 M acetic acid (0.517 g, 8.61 mmol in 43.1 ml water) to 0.2 M sodium acetate (1.641 g, 20.0 mmol in 100 ml water). [[(2,6-Difluorophenyl)carbonyl](1-{[2-fluoro-6-(trifluoromethyl)phenyl]methyl}-1H-pyrazol-4-yl)amino]methyl bis(1,1-dimethylethyl)phosphate (for a preparation see intermediate 4; 86.4 mg, 0.139 mmol) was dissolved in isopropanol (0.75 ml) and pH 5 aqueous buffer solution (0.75 ml) was added. The mixture was heated to 50° C. for 5 hours and then the temperature was increased to 60° C. for a further 4 hours. The reaction was allowed to cool to ambient temperature and half of the solution (750 µl) was adjusted to pH 14 with 5 M aqueous sodium hydroxide (75 µl). This sample was then purified by MDAP (Method E) on Xbridge column using acetonitrile-water with an ammonium carbonate modifier. The product containing fractions were stored in a refrigerator overnight and then the solvent was removed from the combined fractions by freeze-drying to give the title product (21.4 mg) as a white solid; LCMS (System 7): MH$^+$=510, t$_{RET}$=0.64 min.

The remaining half of the reaction solution was left to stand at ambient temperature overnight. 5 M aqueous sodium hydroxide (100 µl) was then added to adjust to pH 14. This sample was then purified by MDAP (Method E) on Xbridge column using acetonitrile-water with an ammonium carbonate modifier. The solvent was removed from the combined product containing fractions by freeze-drying to give the title product (22.8 mg) as a white solid, which was determined to be in the form of a mixed sodium and ammonium salt. LCMS (System 7): MH$^+$=510, t$_{RET}$=0.64 min; $^1$H NMR (DMSO-d$_6$, 600 MHz) δ (ppm) 7.65 (s, 1H), 7.52-7.58 (m, 2H), 7.49 (s, 1H), 7.36-7.41 (m, 1H), 7.21-7.29 (m, 1H), 6.77 (t, J=8.3 Hz, 2H), 5.40 (d, J=7.9 Hz, 2H), 5.35 (s, 2H).

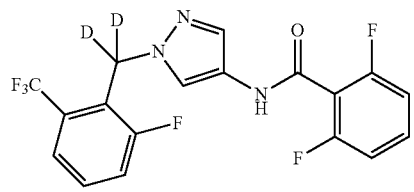 [SMILES: [2H]C([2H])(c1c(F)cccc1C(F)(F)F)n1cc(NC(=O)c2c(F)cccc2F)cn1]

Example 29

2,6-Difluoro-N-(1-(2-fluoro-6-(trifluoromethyl)-d$_2$-benzyl)-1H-pyrazol-4-yl)benzamide 2,6-Difluoro-N-(1H-pyrazol-4-yl)benzamide (for a preparation see intermediate 2; 82 mg, 0.366 mmol) and potassium carbonate (63.2 mg, 0.457 mmol) were weighed into a RBF. A solution of 2-(bromo-d$_2$-methyl)-1-fluoro-3-(trifluoromethyl)benzene (for a preparation see intermediate 16; 79 mg, 0.305 mmol) in DMF (5 mL) was then added and the solution was stirred vigorously under nitrogen at ambient temperature. After 72 hours LCMS indicated that no bromide starting material remained. The reaction mixture was partitioned between ethyl acetate (50 mL) and water (50 mL). The organic layer was then washed twice with water (2×30 mL), dried (sodium sulfate) and evaporated to give a crude product. This sample was dissolved in 1:1 DMSO:methanol (2 mL) and purified by MDAP Sunfire C18 column (Method B) using acetonitrile-water with a formic acid modifier (2×1 mL injections). The product containing fractions were combined and partitioned between saturated aqueous sodium bicarbonate and TBME. The aqueous layer was extracted with further TBME and the combined organic extracts were dried (sodium sulfate) and evaporated to give the title product (56.3 mg, 46%) as a white solid. LCMS (System 3): MH$^+$=402, t$_{RET}$=1.02 min; $^1$H NMR (DMSO-d$_6$, 400 MHz): δ (ppm) 10.81 (s, 1H), 8.02 (s, 1H), 7.74-7.61 (m, 3H), 7.61-7.52 (m, 1H), 7.46 (s, 1H) and 7.22 (t, J=8.1 Hz, 2H).

Biological Experimental

The compounds can be tested according to the following or similar procedures.

This ICRAC assay uses the SERCA inhibitor thapsigargin to produce calcium depletion and activate an ICRAC current. The cells are incubated in a calcium-free environment, thus ionic movement does not occur until the calcium is added back and subsequently enters the cell via the open channels. Changes in intracellular calcium levels are determined by the inclusion of the calcium sensitive fluorescent dye Fluo-4 and the use of the FLIPR detection system. Inhibitors of ICRAC would be expected to decrease the calcium influx upon calcium add-back, thus reducing fluorescent signal.

Jurkat E6-1 is an established immortalised T lymphocyte cell line previously shown to express a functional ICRAC current. Jurkat cells grow in suspension, are cultured in DMEM+10% FBS, maintained in T175 flasks at 37° C./5% CO$_2$, and are subcultured twice a week with either 1:10-1:20 splits. 1 confluent T175 yields 100 ml of approximately 2×10$^6$ cells/ml.

Loading buffer contains; NaCl 145 mM, KCl 2.5 mM, HEPES 10 mM, Glucose 10 mM, MgCl$_2$ 1.2 mM, made up with water, then pH adjusted to 7.4 using NaOH 1 M. Finally Fluo-4AM & brilliant black are added to give a final assay concentration of 2 µM and 250 µM respectively.

Test buffer contains thapsigargin to give a final assay concentration of 5 µM, and test ICRAC inhibitor to give a final assay concentration of 15 µM to 14 µM. In instances of $pIC_{50}$<4.8, compounds of the invention could be screened at a maximum concentration of either 50 µM or 150 µM.

The required seeding density for a 384 plate is 20,000 cells per well. Cells are plated onto a 384 well plate, and loading buffer is added before being incubated at room temperature for 2.5 hours. Subsequently, test buffer is added to the cell plate and incubated at room temperature for a further 10 minutes. Plates are then transferred to the FLIPR which initially measures baseline fluorescence, followed by any increase in fluorescence evoked by the online addition of a 6 mM (1.2 mM FAC) calcium solution.

Fluorescence in the absence of ICRAC inhibitor gives a 100% maximal signal, and increasing concentrations of an ICRAC inhibitor result in a decreased fluorescence signal which is expressed as a percentage inhibition of maximal signal. From the concentration-response relationship, the concentration producing a 50% inhibition of the maximal signal ($pIC_{50}$) can then be determined.

Examples 1-27 were tested in the above assay, and were found to have a $pIC_{50} \geq 5.1$ and $\leq 6.0$ with the exception of examples 7, 11, 18 and 24 which had a $pIC_{50}$<5.0.

Examples 1-4, 6, 8, 9, 12, 16, 17, 19, 26 and 27 were found to have a $pIC_{50} \geq 5.5$ and 6.0.

In Vitro Microsomal Clearance for Examples 6 and 29

| $Cl_{int}$ (mL/min g liver) | Example 6 | Example 29 |
|---|---|---|
| Human | 0.80 | <0.5 |
| Rat (CD) | 1.67 | 0.95 |
| Dog (Beagle) | 0.98 | 0.80 |
| Rat (Wistar Han) | 2.05 | 1.16 |

The invention claimed is:

1. A compound of formula (I) thereof in which $R^a$ is a group of formula (a1)

in which $R^{1a}$ is $CF_3$, $OCF_3$, $C_{1-6}$alkoxy or $R^{1a}$ is a group $L^1$-$Z^1$ in which $L^1$ is a bond, O, $CH_2$, $OCH_2$ or $CH_2O$ and $Z^1$ is aryl;

or $R^a$ is a group of formula (a2)

in which
$R^{2a}$ is halogen or $OCH_2Ph$; and
$R^{3a}$ is Cl or Br;
or $R^a$ is a group of formula (a3)

in which
$R^{4a}$ is $C_{1-6}$alkoxy, $CF_3$ or $OCH_2Ph$; and
$R^{5a}$ is halogen;
or $R^a$ is a group of formula (a4)

in which
$R^{6a}$ is F, Br or $CF_3$;
$R^b$ is a group of formula (b)

wherein
Y is CH,
$R^{1b}$ is halogen;
$R^{2b}$ is H, halogen or $C_{1-3}$alkyl;
or a salt thereof.

2. A compound or a salt thereof according to claim 1 wherein $R^a$ is a group of formula (a1) in which $R^{1a}$ is a group $L^1$-$Z^1$ wherein $L^1$ is as defined in claim 1 and $Z^1$ is phenyl.

3. A compound or a salt thereof according to claim 1 wherein $R^a$ is a group of formula (a2) in which $R^{2a}$ and $R^{3a}$ are both chloro.

4. A compound or a salt thereof according to claim 1 wherein $R^a$ is a group of formula (a3) in which $R^{4a}$ is $OCH_2Ph$ and $R^{5a}$ is halogen.

5. A compound or a salt thereof according to claim 1 wherein $R^a$ is a group of formula (a4) in which $R^{6a}$ is $CF_3$.

6. A compound or a salt thereof according to claim 1 wherein $R^b$ is a group of formula (b) in which $R^{1b}$ and $R^{2b}$ are both fluoro.

7. A compound selected from the group consisting of
2,6-Difluoro-N-(1-{[2-(phenyloxy)phenyl]methyl}-1H-pyrazol-4-yl)benzamide;
2,6-Difluoro-N-[1-({2-[(trifluoromethyl)oxy]phenyl}methyl)-1H-pyrazol-4-yl]benzamide;
2,6-Difluoro-N-[1-({2-[(phenylmethyl)oxy]phenyl}methyl)-1H-pyrazol-4-yl]benzamide;
N-[1-(2-Biphenylylmethyl)-1H-pyrazol-4-yl]-2,6-difluorobenzamide;
2,6-Difluoro-N-(1-{[2-(trifluoromethyl)phenyl]methyl}-1H-pyrazol-4-yl)benzamide;
2,6-Difluoro-N-(1-{[2-fluoro-6-(trifluoromethyl)phenyl]methyl}-1H-pyrazol-4-yl)benzamide;
N-{1-[(4-Chloro-2-fluorophenyl)methyl]-1H-pyrazol-4-yl}-2,6-difluorobenzamide;
N-[1-({5-Chloro-2-[(2-methylpropyl)oxy]phenyl}methyl)-1H-pyrazol-4-yl]-2,6-difluorobenzamide;
N-[1-({5-Bromo-2-[(phenylmethyl)oxy]phenyl}methyl)-1H-pyrazol-4-yl]-2,6-difluorobenzamide;
2,6-Difluoro-N-(1-{[5-fluoro-2-(trifluoromethyl)phenyl]methyl}-1H-pyrazol-4-yl)benzamide;
N-(1-{[5-Chloro-2-(methyloxy)phenyl]methyl}-1H-pyrazol-4-yl)-2,6-difluorobenzamide;
2,6-difluoro-N-(1-(2-methoxybenzyl)-1H-pyrazol-4-yl)benzamide;
N-(1-{[2-(Butyloxy)phenyl]methyl}-1H-pyrazol-4-yl)-2,6-difluorobenzamide;
2,6-Difluoro-N-[1-({2-[(phenyloxy)methyl]phenyl}methyl)-1H-pyrazol-4-yl]benzamide;
N-[1-({4-Chloro-2-[(phenylmethyl)oxy]phenyl}methyl)-1H-pyrazol-4-yl]-2,6-difluorobenzamide;
2,6-Difluoro-N-(1-{[2-(phenylmethyl)phenyl]methyl}-1H-pyrazol-4-yl)benzamide;
2,6-Dichloro-N-{1-[(2,4-dichlorophenyl)methyl]-1H-pyrazol-4-yl}benzamide;
2-Chloro-N-{1-[(2,4-dichlorophenyl)methyl]-1H-pyrazol-4-yl}-6-fluorobenzamide;
N-{1-[(2,4-Dichlorophenyl)methyl]-1H-pyrazol-4-yl}-3-fluoro-4-pyridinecarboxamide;
2,6-Dibromo-N-{1-[(2,4-dichlorophenyl)methyl]-1H-pyrazol-4-yl}benzamide;
2-Bromo-6-chloro-N-{1-[(2,4-dichlorophenyl)methyl]-1H-pyrazol-4-yl}benzamide;
2-Bromo-N-{1-[(2,4-dichlorophenyl)methyl]-1H-pyrazol-4-yl}-6-fluorobenzamide;
N-{1-[(2,4-Dichlorophenyl)methyl]-1H-pyrazol-4-yl}-3,5-difluoro-4-pyridinecarboxamide;
N-{1-[(2,4-Dichlorophenyl)methyl]-1H-pyrazol-4-yl}-2,6-difluorobenzamide;
2-Chloro-N-{1-[(2,4-dichlorophenyl)methyl]-1H-pyrazol-4-yl}-6-methylbenzamide;
N-{1-[(2,4-Dichlorophenyl)methyl]-1H-pyrazol-4-yl}-2-fluorobenzamide;
2-Chloro-N-[1-({5-chloro-2-[(phenylmethyl)oxy]phenyl}methyl)-1H-pyrazol-4-yl]-6-fluorobenzamide;
N-[1-({5-Chloro-2-[(phenylmethyl)oxy]phenyl}methyl)-1H-pyrazol-4-yl]-2,6-difluorobenzamide;
[[(2,6-Difluorophenyl)carbonyl](1-{[2-fluoro-6-(trifluoromethyl)phenyl]methyl}-1H-pyrazol-4-yl)amino]methyl dihydrogen phosphate;
2,6-Difluoro-N-(1-(2-fluoro-6-(trifluoromethyl)-$d_2$-benzyl)-1H-pyrazol-4-yl)benzamide;
or a salt thereof.

8. A pharmaceutical composition comprising a compound as defined in claim 1, or a pharmaceutically acceptable salt, thereof and one or more pharmaceutically acceptable carriers, diluents or excipients.

9. A combination comprising a compound as defined in claim 1, or a pharmaceutically acceptable salt thereof, and one or more other therapeutic compounds chosen from a $\beta_2$-adrenoreceptor agonist, corticosteroid, NSAID's, PDE4 inhibitor, anticholinergic, antihistamine, or another calcium release activated calcium channel inhibitor.

10. A pharmaceutical composition comprising a compound as defined in claim 7, or a pharmaceutically acceptable salt, thereof and one or more pharmaceutically acceptable carriers, diluents or excipients.

* * * * *